(12) United States Patent  
Mitsunaga

(10) Patent No.: US 8,968,184 B2  
(45) Date of Patent: Mar. 3, 2015

(54) ENDOSCOPE APPARATUS, FOLDER GENERATING METHOD, AND NON-TRANSITORY COMPUTER READABLE RECORDING MEDIUM

(71) Applicant: Olympus Corporation, Tokyo (JP)

(72) Inventor: Osamu Mitsunaga, Kokubunji (JP)

(73) Assignee: Olympus Corporation, Tokyo (JP)

( * ) Notice: Subject to any disclaimer, the term of this patent is extended or adjusted under 35 U.S.C. 154(b) by 4 days.

(21) Appl. No.: 13/709,442

(22) Filed: Dec. 10, 2012

(65) Prior Publication Data

US 2013/0345502 A1  Dec. 26, 2013

(30) Foreign Application Priority Data

Jun. 20, 2012  (JP) .................................. 2012-138991

(51) Int. Cl.
| | | |
|---|---|---|
| *A61B 1/04* | (2006.01) | |
| *A61B 1/06* | (2006.01) | |
| *A61B 1/00* | (2006.01) | |
| *G02B 23/24* | (2006.01) | |
| *G11B 27/10* | (2006.01) | |
| *G11B 27/34* | (2006.01) | |
| *H04N 5/225* | (2006.01) | |

(52) U.S. Cl.
CPC ................ *A61B 1/0002* (2013.01); *A61B 1/04* (2013.01); *A61B 1/00045* (2013.01); *G02B 23/2476* (2013.01); *G11B 27/105* (2013.01); *G11B 27/34* (2013.01); *G05B 2219/31316* (2013.01); *H04N 2005/2255* (2013.01)
USPC ............................ 600/109; 600/160; 600/118

(58) Field of Classification Search
CPC ............. A61B 1/0009; A61B 1/00045; A61B 1/00039; G06F 19/321; G06F 19/3406; G06F 19/3487; G06F 17/30247; G06F 17/30011

USPC ................ 600/102, 117, 118, 109, 160, 424; 348/65

See application file for complete search history.

(56) References Cited

U.S. PATENT DOCUMENTS

| | | | | |
|---|---|---|---|---|
| 5,943,093 | A * | 8/1999 | Anderson et al. | .......... 348/231.6 |
| 8,217,646 | B2 * | 7/2012 | Karpen | .......... 324/228 |
| 2004/0008223 | A1 * | 1/2004 | Britton et al. | .......... 345/762 |
| 2007/0130190 | A1 * | 6/2007 | Yoshikawa | .......... 707/102 |
| 2007/0225931 | A1 | 9/2007 | Morse et al. | |
| 2007/0226258 | A1 * | 9/2007 | Lambdin et al. | .......... 707/104.1 |
| 2008/0304724 | A1 * | 12/2008 | Eino | .......... 382/128 |
| 2012/0300997 | A1 * | 11/2012 | Li | .......... 382/128 |
| 2013/0097171 | A1 * | 4/2013 | Weksler et al. | .......... 707/740 |

FOREIGN PATENT DOCUMENTS

| | | | |
|---|---|---|---|
| JP | 2006-276991 A | 10/2006 | |
| JP | 2011-165154 A | 8/2011 | |

* cited by examiner

*Primary Examiner* — Anhtuan T Nguyen  
*Assistant Examiner* — William Chou  
(74) *Attorney, Agent, or Firm* — Holtz, Holtz, Goodman & Chick PC

(57) ABSTRACT

An endoscope apparatus comprises an analyzing portion configured, in a folder generating mode for extracting folder generating information regarding generation of a plurality of folders that record a plurality of image data of an inspection object, to analyze an image picked up by an image pickup portion and to extract the folder generating information; a folder generating portion configured to generate a plurality of folders regarding the inspection object based on the folder generating information extracted by the analyzing portion; and an inspection image recording portion configured to record each image data of the inspection object picked up by the image pickup portion in one folder among the plurality of folders generated by the folder generating portion.

7 Claims, 22 Drawing Sheets

ENGINE1_SN001_HPC_STAGE1_ZONE1_1_A_001.jpg
⎵ 81 ⎵  ⎵ 82 ⎵  83 84 85

FIG.18

| Area | Block Location | Reason for Inspection | Outcome | Picture |
|---|---|---|---|---|
| HPC | STAGE1_ZONE1 | Cracks | Accept | *111* |
| | | | Accept | *112* |
| HPC | STAGE1_ZONE1 | Surface Defects | Re-Inspect Some Defects | *113* |
| HPC | STAGE1_ZONE2 | Cracks | Reject Cracks | *114* |

FIG.24

| | Area | Block Location | Reason for Inspection | Outcome | Picture |
|---|---|---|---|---|---|
| | | | | | |
| 111 | ⟨AREA1⟩ | ⟨LOCATION1⟩ | ⟨INSPECTION1⟩ | ⟨JUDGEMENT1⟩<br>⟨TITLE1⟩ | ⟨PIC1⟩ |
| 112 | ⟨AREA2⟩ | ⟨LOCATION2⟩ | ⟨INSPECTION2⟩ | ⟨JUDGEMENT2⟩<br>⟨TITLE2⟩ | ⟨PIC2⟩ |
| 113 | ⟨AREA3⟩ | ⟨LOCATION3⟩ | ⟨INSPECTION3⟩ | ⟨JUDGEMENT3⟩<br>⟨TITLE3⟩ | ⟨PIC3⟩ |

106a: ENGINE1_SN001

| Area | Block Location | Reason for Inspection | Outcome | Picture |
|---|---|---|---|---|
| HPC | STAGE_ZONE2 | Cracks | Reject Cracks ⋮ | 114 |
| HPC | STAGE_ZONE1 | Cracks | Accept | 111 |
| | | | Accept | 112 |
| HPC | STAGE_ZONE1 | Surface Defects | Re-Inspect Some Defects ⋮ | 113 |

ENGINE1 SN001

ENDOSCOPE APPARATUS, FOLDER GENERATING METHOD, AND NON-TRANSITORY COMPUTER READABLE RECORDING MEDIUM

CROSS REFERENCE TO RELATED APPLICATION

This application claims benefit of Japanese Application No. 2012-138991 filed in Japan on Jun. 20, 2012, the contents of which are incorporated by this reference.

BACKGROUND OF THE INVENTION

1. Field of the Invention

The present invention relates to an endoscope apparatus, a folder generating method and a non-transitory computer readable recording medium.

2. Description of the Related Art

Endoscope apparatuses are widely used in medical and industrial areas. The endoscope apparatus typically includes an insertion portion to be inserted into an object and a main body having a display portion for displaying an observation image obtained by photographing the inside of the object. The endoscope apparatus is used in the industrial area to inspect internal scratches and corrosion by inserting the elongated insertion portion into the inside of a boiler, a turbine, an engine, etc. In the gazette of U.S. Patent Application Publication No. 2007/0225931, the technology of recording an image, which is an inspected image, in a plurality of folders is described.

In Japanese Patent Application Laid-Open Publication No. 2011-165154, the technology of generating measured data by a QR Code, which is a two-dimensional barcode, in a measured value management system is described.

SUMMARY OF THE INVENTION

The present invention provides an endoscope apparatus, a folder generating method and a non-transitory computer readable recording medium.

The endoscope apparatus in the present invention includes an image pickup portion; an analyzing portion configured to extract folder generating information regarding generation of a plurality of folders from an image obtained by the image pickup portion in a first mode; a folder generating portion configured to generate the plurality of folders regarding the inspection object based on the folder generating information extracted by the analyzing portion; and an image recording portion configured to record the plurality of image data of the inspection object, each image data of the inspection object obtained by the image pickup portion being recorded in a designated folder of the plurality of folders generated by the folder generating portion in a second mode.

BRIEF DESCRIPTION OF THE DRAWINGS

The above features and advantages of the present invention will be more apparent from the following description of certain preferred embodiments taken in conjunction with the accompanying drawings, in which:

FIG. 18 is a diagram for explaining an example of the composition of an endoscope inspection report in accordance with the embodiment of the present invention.

FIG. 24 is a diagram for explaining an example of a report template included in a QR code in accordance with a modification of the embodiment of the present invention.

FIG. 26 is a diagram for explaining an example of the structure of an endoscope inspection report generated with report template information in FIG. 24 and attachment sequence information TBL in FIG. 25 in accordance with the modification of the embodiment of the present invention.

DETAILED DESCRIPTION OF THE PREFERRED EMBODIMENT

Hereafter, referring to drawings, embodiments of the present invention will be described. It will be obvious to those skilled in the art, based on the disclosed contents, that the following description of the embodiments of the present invention merely describes the invention defined in the attached claims and its equivalents in detail, not intending to limit them.
(General Configuration)

Figure 1:
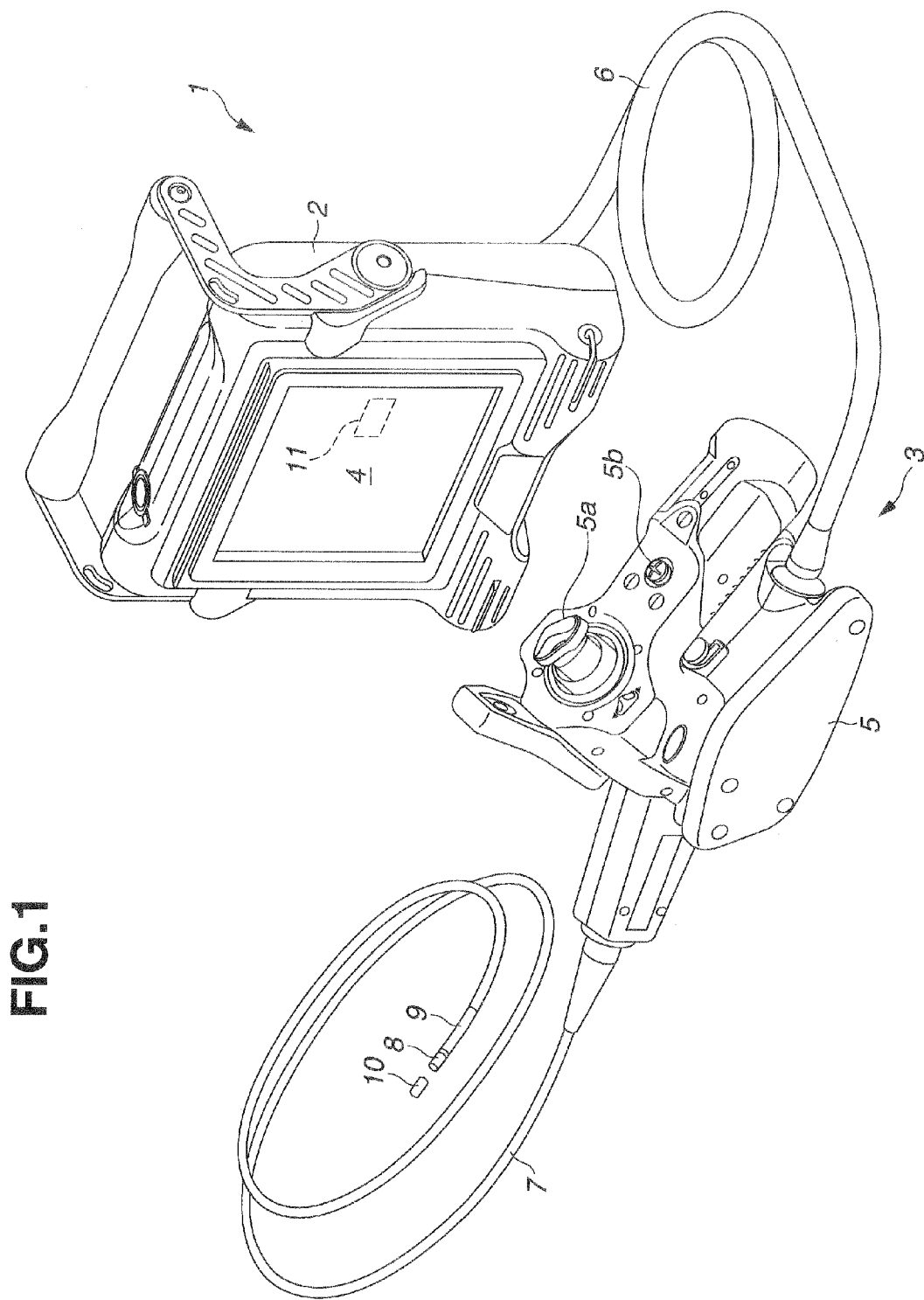
FIG. 1 is an external configuration diagram of an endoscope system 1 in accordance with an embodiment of the present invention.

FIG. 1 is an external configuration diagram of an endoscope system 1 in accordance with an embodiment of the present invention.

As shown in FIG. 1, the endoscope system 1 is configured by comprising a main body 2 as a main unit and a scope unit 3 connected to the main body 2. The main body 2 has a liquid crystal panel (hereinafter abbreviated as LCD) as a display device on which endoscope images, control menus, etc. are displayed. The LCD 4 is a display portion for displaying endoscope images. As described later, a touch panel (FIG. 2) may be provided on the LCD 4. The scope unit 3 has an operation unit 5, a universal cable 6 connecting the operation unit 5 and the main body 2, and an insertion portion 7 consisting of a flexible insertion portion. The scope unit 3 is attachable/detachable to and from the main body 2. A distal end portion 8 of the insertion portion 7 has a built-in image pickup unit (FIG. 2) as described later. The image pickup unit consists of an image pickup device, for example, a CCD sensor, a CMOS sensor, or the like and an image pickup optical system such as a lens disposed on the image pickup surface side of the image pickup device. On a proximal end side of the distal end portion 8, a bending portion 9 is provided. To the distal end portion 8, an optical adapter 10 is attachable. In the operation portion 5, various operation buttons are provided such as a freeze button and a recording instruction button (hereinafter referred to as REC button).

A user may perform image-picking up of an object, recording of a still image, etc. by operating various operation buttons in the operation unit 5. A user may bend the bending portion 9 in any desired direction by operating an Up/Down/Left/Right (U/D/L/R) bending button 5a. Further, a user may select a recording destination folder by operating a joystick 5b provided in the operation unit 5 to incline in any of U/D/L/R directions when the recording destination folder of an endoscope image as described later is changed. Also, if the structure is such that a touch panel is provided on the LCD 4, a user may give instructions of various operations of the endoscope system 1 by operating the touch panel. In other words, the touch panel constitutes an instruction portion for instructing operations of the endoscope system 1.

Image data of the endoscope images obtained by image pickup are inspected data of an inspection object, which will be recorded in a memory card 11 being a recording medium. The memory card 11 is attachable/detachable to and from the main body 2. In the memory card 11, a plurality of folders for recording image data of endoscope images are stored. A plurality of folders corresponding to the inspection object are generated as described later and stored in the memory card 11.

Incidentally, although a plurality of folders and image data are stored in the memory card 11 as a recording medium detachable from the main body 2 in the embodiment of the present invention, those may be recorded in a memory built in the main body 2.

A user brings the distal end portion 8 of the insertion portion 7 close to an inspection region of an inspection object and photographs the inspection region. The LCD 4 displays the endoscope image photographed. Further, as described later, the user may change a recording destination folder of an endoscope image while confirming a folder in the memory card 11 for recording an endoscope image during inspection and by operating the operation portion 5 if necessary.
(Circuit Configuration)

Figure 2:
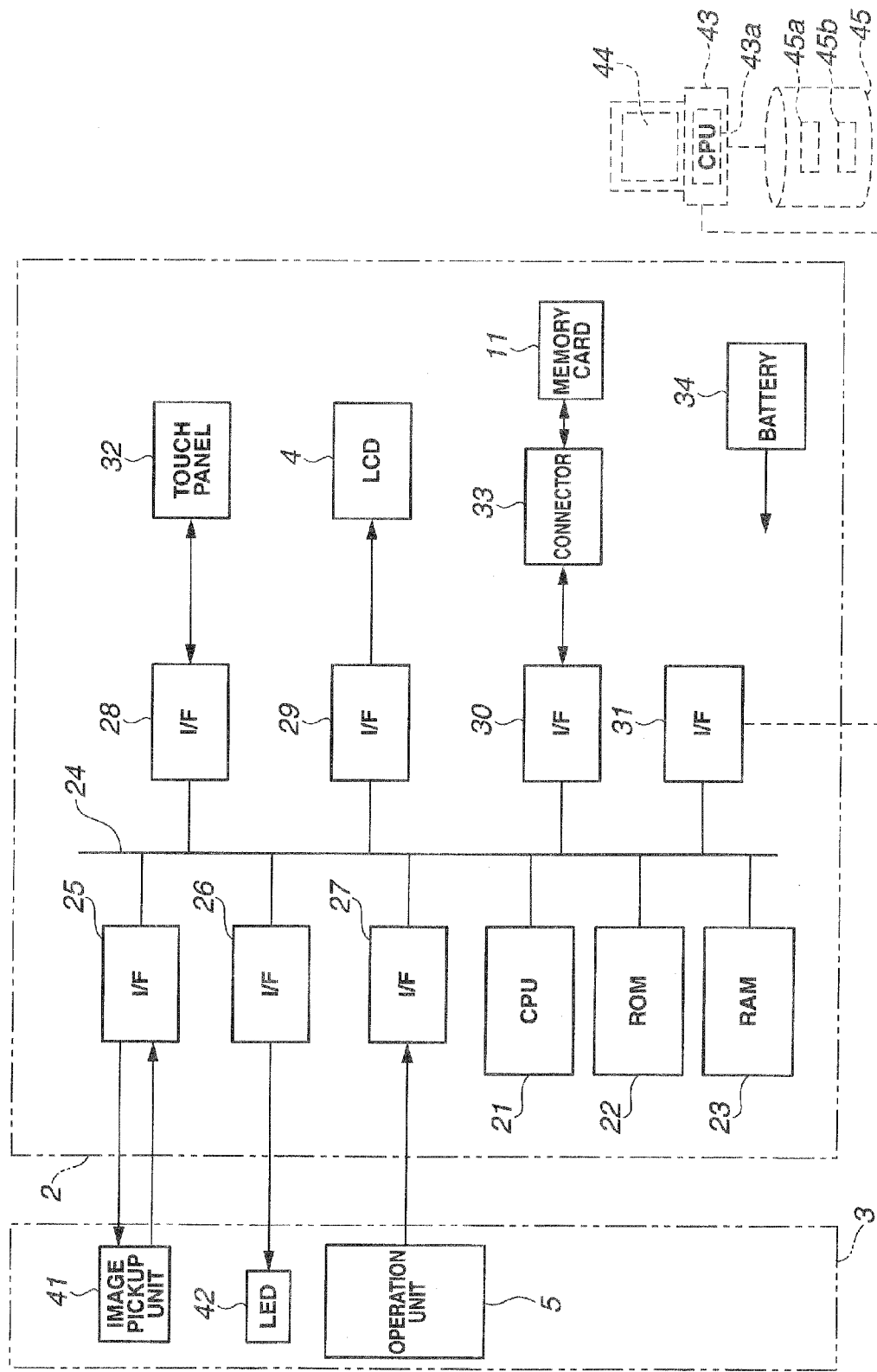
FIG. 2 is a block diagram for explaining internal circuit configuration of a main body 2 of the endoscope system 1 in accordance with the embodiment of the present invention.

FIG. 2 is a block diagram for explaining internal circuit configuration of the main body 2 of the endoscope system 1.

The main body 2 includes a central processing unit (hereinafter referred to as CPU) 21, a ROM 22 and a RAM 23, being mutually connected via a bus 24. Further, to the bus 24, a plurality of different kinds of interfaces (hereinafter referred to as I/Fs) 25 to 31 are connected. The I/F 25 is a driving and receiving circuit for transmitting driving signals to an image pickup unit 41 of the scope unit 3 and receiving image pickup signals from the image pickup unit 41. The I/F 26 is a driving circuit for transmitting driving signals to an LED 42 as an illuminating unit.

The I/F 27 is a circuit for receiving various operating signals from the operation unit 5. An operating signal of the joystick 5b is included in various operating signals from the operation unit 5. If the structure is such that a touch panel 32 is provided on the LCD 4, the I/F 28 will be provided as a circuit for transmitting driving signals to the touch panel 32 and receiving operating signals from the touch panel 32. The I/F 29 is a circuit for providing image signals to the LCD 4.

The I/F 30 is a circuit for writing image signals to the memory card 11 and reading image signals from the memory card 11. The I/F 30 is connected to the memory card 11 via a connector 33 provided in the main body 2. The memory card 11 is attached to the connector 33 detachably.

The I/F 31 is a circuit for connecting a personal computer (hereinafter referred to as PC) 43, which is an external device, to the main body 2. The PC 43 is connected to the main body 2 via an unillustrated connector, and the main body 2 may exchange data with the PC 43 via the I/F 31 connected to that connector.

As shown in dotted lines, the PC 43 has a CPU 43a and a monitor 44, to which a storage device 45 is connected. A report generating program 45a as described later is stored in the storage device 45, and a report generated by the report generating program 45a is either displayed on the monitor 44 or output by an unillustrated printer. The storage device 45 further includes a template storage unit 45*b* for storing template information to be utilized during report generation as described later.

The main body 2 has a built-in battery 34 inside, and the battery 34 provides electric power to various circuits in the main body 2.

Each of the I/Fs operates under the control of the CPU 21. When the endoscope system 1 is started up, the CPU 21 outputs drive instructing signals of the LED 42 to the I/F 26. Driven by the output of the I/F 26, the LED 42 illuminates the object. Then, the CPU 21 outputs various driving signals to the image pickup unit 41 via the I/F 25. The image pickup unit 41 outputs imaging signals to the CPU 21. As a result, a live image is displayed on the LCD 4.

The operation unit 5 provides various operating signals to the CPU 21 indicating the contents of operation to the operation unit 5 by a user. When a user presses the freeze button as described later, the CPU 21 generates a still image based on image pickup signals from the image pickup unit 41. Further, when a user presses the REC button, the image data of the still image is recorded in the memory card 11. Because the still image by freezing is displayed on the LCD 4, the user may once confirm the frozen still image. Then, if the still image is to be recorded by the user, the REC button will be pressed.

Further, various programs according to various modes are stored in the ROM 22. The CPU 21 is structured to be capable of reading from the ROM 22 and run a corresponding program in response to the instruction by the user as an inspector. The endoscope system 1 has also another mode in addition to the endoscope inspection mode, which is a mode at the time of performing a typical endoscope inspection. As another mode, there is a folder generating mode for storing image data of endoscope images. As described below, the user may automatically generate in the memory card 11 a plurality of folders corresponding to the inspection object by executing the folder generating mode.

(Generation of Folder)

The name and configuration of an inspection object vary with each inspection object. For example, the name and configuration of an inspection object are different between an aircraft engine and a piping system and also different between manufacturers, models, etc. even for an aircraft engine.

In the embodiment of the present invention, the endoscope system 1 is configured so that a folder for an inspection image suitable for different inspection objects may be generated, for example, at the inspection site where an inspection object is to be inspected.

Figure 3:
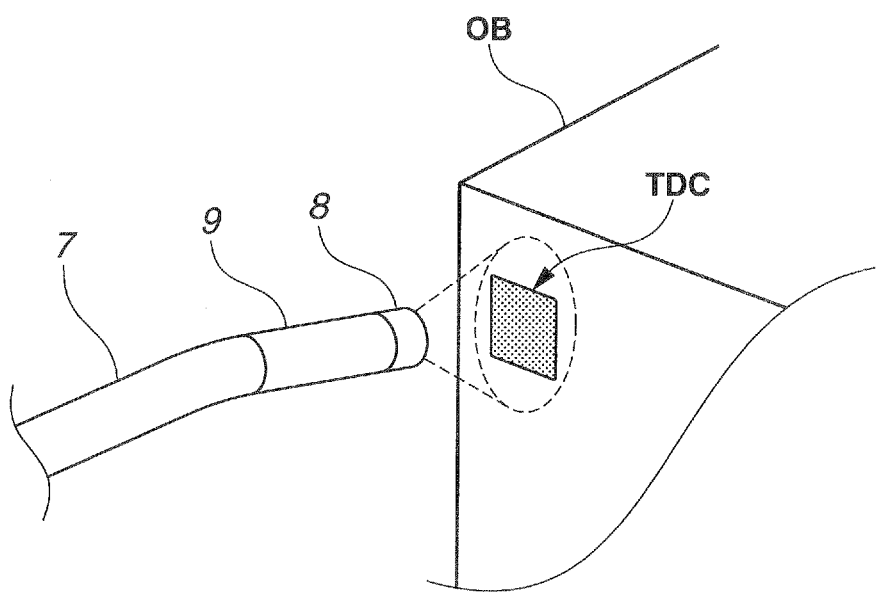
FIG. 3 is a diagram for explaining the case of an image of a two-dimensional code being photographed when a plurality of folders are generated corresponding to an inspection object in accordance with the embodiment of the present invention.

In the embodiment of the present invention, a plurality of folders for storing inspected images of an inspection object are generated by image-picking up the two-dimensional code attached to the inspection object with the image pickup unit 41, which is an image pickup portion of the endoscope system 1. FIG. 3 is a diagram for explaining the case of an image of a two-dimensional code being photographed when a plurality of folders are generated corresponding to the inspection object.

A user sets the endoscope system 1 to a folder generating mode, which is a mode for generating a plurality of folders on the inspection object, by operating the predetermined button etc. of the operation unit 5. Then, the user brings the distal end portion 8 of the insertion portion 7 close to a QR code TDC and picks up an image of the QR code TDC. The QR code TDC is printed, for example, on a sticker or a sheet of paper and attached on a housing OB etc. of the inspection object. The QR code is inspection object identifying information, including folder generating information. When the folder generating mode is set, the endoscope system 1 executes generation processing of a folder. The folder generating mode is a mode for extracting the folder generating information on generation of a plurality of folders for recording a plurality of image data of the inspection object. As described later, a plurality of folders concerning the inspection object are generated, based on the folder generating information obtained as a result of analyzing the QR code.

Figure 4:
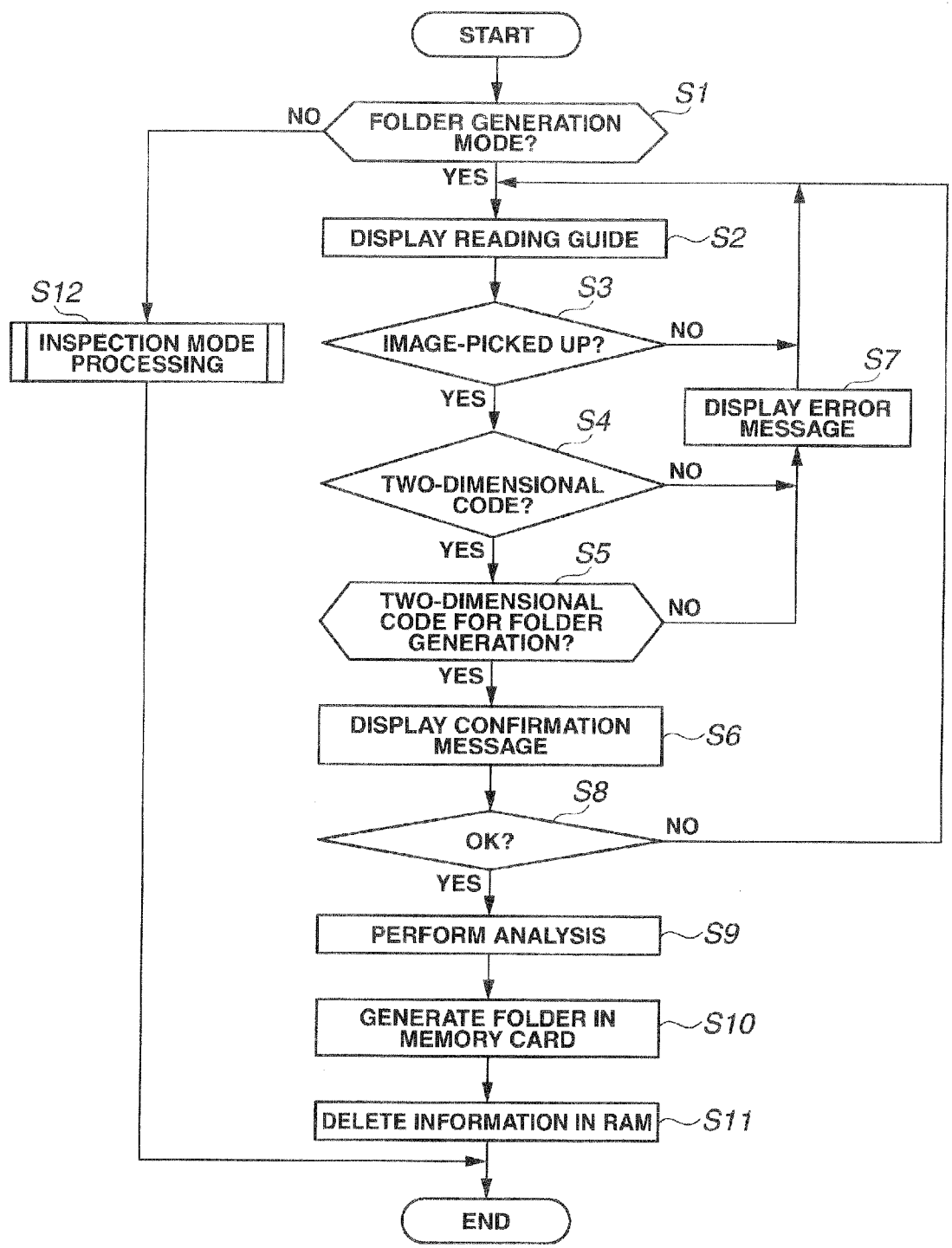
FIG. 4 is a flowchart illustrating an example of process flow when a folder generating mode has been designated for the endoscope system 1 in accordance with the embodiment of the present invention.

Next, generation processing of a folder will be described. As described above, there is a folder generating mode in a plurality of operation modes included in the endoscope system 1. The user may cause the endoscope system 1 to operate in a desired operation mode by designating the operation mode. The generation processing of a folder will be executed when the folder generating mode is designated by the user. FIG. 4 is a flowchart illustrating an example of process flow when the folder generating mode has been designated for the endoscope system 1. Incidentally, here the generation processing of a folder will be described by indicating a case where there are two modes, the folder generating mode and a normal endoscope inspection mode, for the purpose of simplifying the description. The folder generating program for processing as shown in FIG. 4 is stored in the ROM 22.

When the user inputs an operation mode to the operation unit 5, the CPU 21 executes processing as shown in FIG. 4. First, whether the input operation mode is the folder generating mode or not is determined (S1).

If the input operation mode is the folder generating mode (S1: YES), the CPU 21 displays a reading guide on the LCD 4 (S2). The reading guide indicates a recommendation range to locate the QR code.

Figure 5:
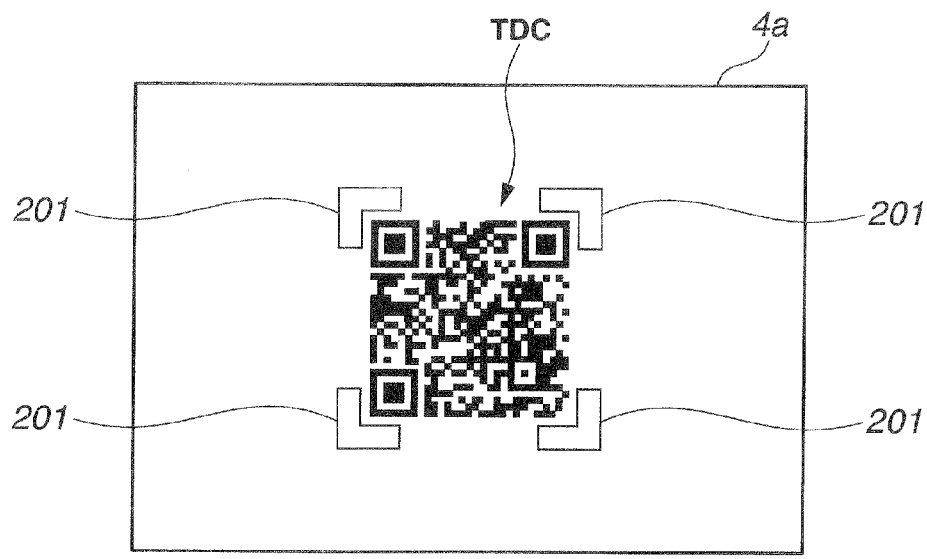
FIG. 5 is a diagram indicating an example of a reading guide displayed on an LCD 4 in accordance with the embodiment of the present invention.

FIG. 5 is a diagram indicating an example of the reading guide displayed on the LCD 4. On a screen 4*a* of the LCD 4, a guide 201 is displayed for indicating a frame for image-picking up the QR code TDC properly, which is inspection object identifying information. Here, the guide 201 consists of four L-shaped patterns to make indicating marks located on four corners of the rectangular QR code TDC. It is preferable to pick up an image of the QR code TDC with the QR code TDC positioned within the area indicated by the four L-shaped patterns.

The S2 processing configures a guiding image display portion displaying a guiding image for obtaining folder generating information by image-picking up with the image pickup portion on the LCD 4 as a displaying unit in the folder generating mode.

Incidentally, although an example that the QR code is adopted as the two-dimensional code is described in the embodiment of the present invention, another code may be adopted. In such a case, a guide suitable for the shape of the other code adopted will be displayed. For example, the guide may be a cross mark, a square mark, etc.

After S2, the CPU 21 determines, for example, whether an image has been recorded by pressing the REC button after pressing the freeze button (S3). If no image is recorded (S3: NO), the processing returns to S2.

If an image is recorded (S3: YES), the CPU 21 determines whether there is a QR code TDC, which is a two-dimensional code, or not in the guide 201 of the recorded image (S4). In S4, whether there is a QR code in the image section of the guide 201 or not is determined by image processing. The recorded image is stored in the RAM 23. Incidentally, in S3 and S4, the CPU 21 may determine the presence of the QR code in a live image without operating the freeze button and the REC button.

If a two-dimensional code, i.e. the QR code is included in the recorded image (S4: YES), the CPU 21 determines whether that particular two-dimensional code is the two-dimensional code, which is attached to the inspection object, for generating a folder, (S5). This is because there may be a case where the QR code included in the recorded image is not the QR code for generating a folder. In S5, whether the QT code included in the recorded image is the QR code for generating a folder containing predetermined information or not is determined by image processing. The QR code for generating a folder includes information for generating a folder. It is possible to make a determination of S5 by distinguishing the presence of information for generating a folder.

If the QR code for generating a folder has been read (S5: YES), the CPU 21 displays, from the information read, the confirmation message indicating the target information on the inspection object included in that information on the screen 4a of the LCD 4 (S6). As target information, the name of the uppermost folder, for example, is displayed on the screen of the LCD 4. If the QR code read is the QR code for generating a folder, a name of the folder is included in the folder generating information that is included in the QR code. Because, for example, the name of the inspection object, the model number, etc. or its abbreviation are included in the name of the uppermost file, the user may identify the inspection object.

Figure 6:
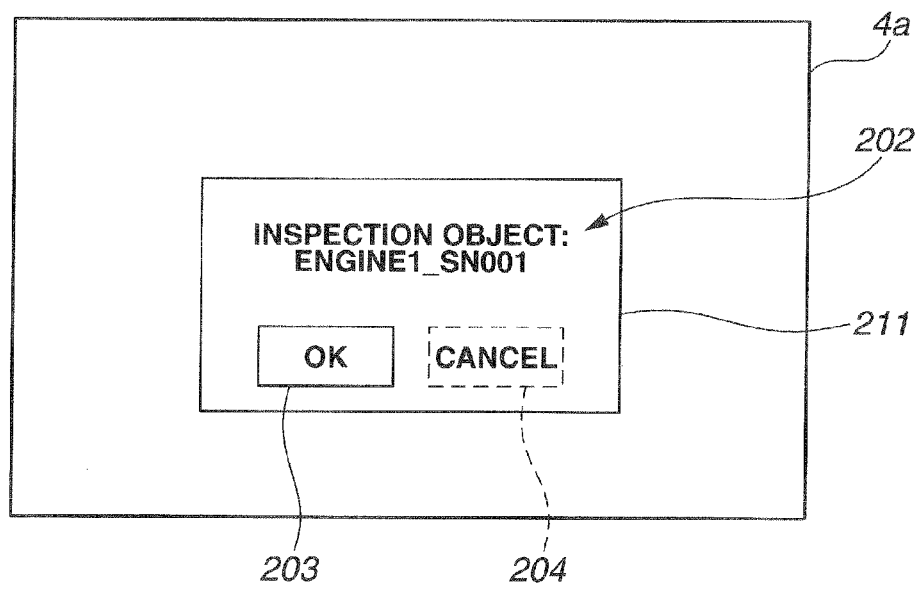
FIG. 6 is a diagram indicating a display example of a confirmation message in accordance with the embodiment of the present invention.

FIG. 6 is a diagram indicating a display example of a confirmation message. A predetermined confirmation message is displayed in the window 211, on the screen 4a of the LCD 4. In FIG. 6, the message "Inspection Object: ENGINE1_SN001" is displayed in the window 211.

Further, the window 211 includes an "OK" button 203 and a "Cancel" button 204. The user may select the "OK" button 203 or the "Cancel" button 204 by performing a predetermined operation in the operation unit 5. Incidentally, because the "OK" button 203 is in the selected state by default in FIG. 6, the "OK" button 203 is displayed more highlightedly than the "Cancel" button 204.

The user selects the "OK" button 203 if the inspection object to be inspected is identical to the inspection object indicated by the information shown in the confirmation message. However, the user selects the "Cancel" button 204 if the inspection object to be inspected is not identical to the inspection object indicated by the information shown in the confirmation message.

Incidentally, if the read image is not a two-dimensional code (S4:NO) or the two-dimensional code is not the QR code for generating a folder (S5:NO), an error message is displayed (S7), and the processing returns to S2. Therefore, the user may perform reading of the QR code again.

Figure 7:
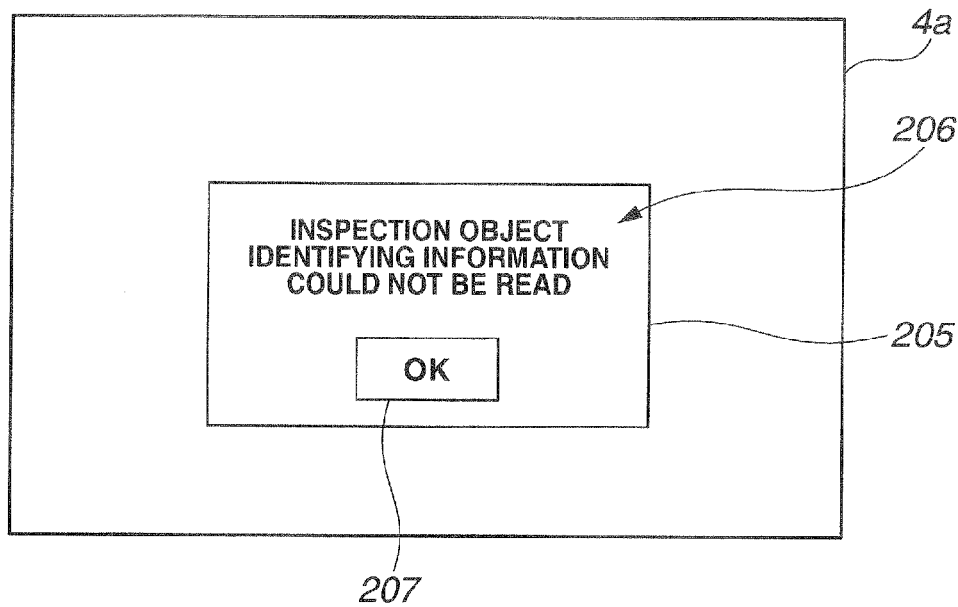
FIG. 7 is a diagram indicating a display example of an error message in accordance with the embodiment of the present invention.

FIG. 7 is a diagram indicating a display example of an error message. On the screen 4a of the LCD 4, a predetermined error message is displayed in a window 205. In FIG. 7, the message 206 reading "Inspection object identifying information could not be read." is displayed in the window 205. The error message in FIG. 7 is an example to be displayed if the image read is not the two-dimensional code.

Further, the window 205 includes an "OK" button 207. The user may select the "OK" button 207 by performing a predetermined operation in the operation unit 5.

The user selects the "OK" button 207, upon confirming that the QR code, which is inspection object identifying information on the inspection object to be inspected, could not be read.

Figure 8:
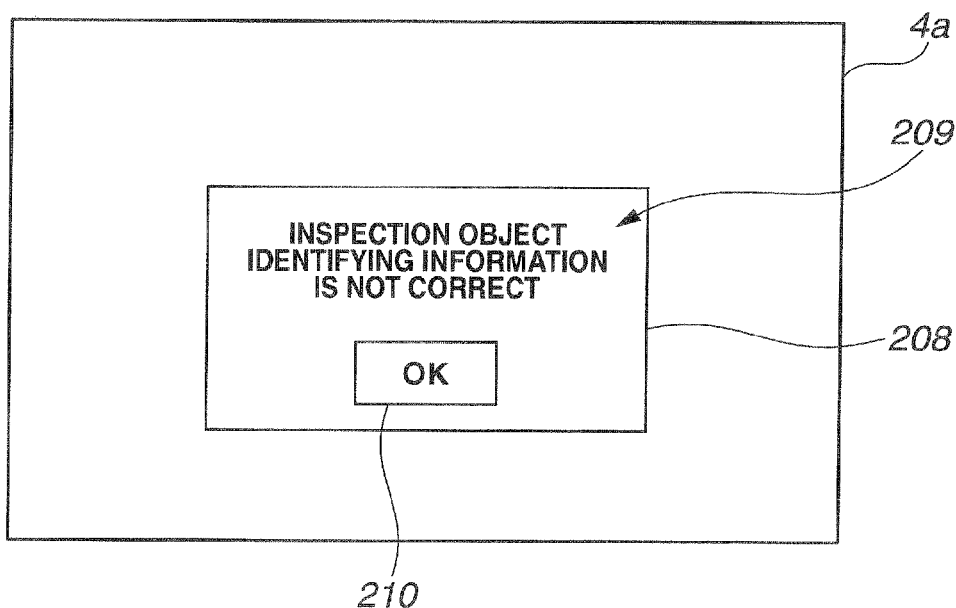
FIG. 8 is a diagram indicating another display example of the error message in accordance with the embodiment of the present invention.

FIG. 8 is a diagram indicating another display example of the error message. On the screen 4a of the LCD 4, a predetermined error message is displayed in a window 208. In FIG. 8, the message 209 reading "Inspection object identifying information is not correct." is displayed in the window 208. The error message in FIG. 8 is an example to be displayed if the QR code read is not the QR code for generating a folder.

Therefore, the S7 processing configures an extracted result display portion for displaying that the folder generating information has not been included in the LCD 4, which is a display portion, if folder generating information has not been included in the image obtained by image-picking up with the image pickup unit 41, which is an image pickup portion, during the folder generating mode.

Further, the window 208 includes an "OK" button 210. The user may select the "OK" button 210 by performing a predetermined operation in the operation unit 5.

After the S6 processing, the CPU 21 determines whether the "OK" button 203 in FIG. 6 has been selected or not (S8). If the "OK" button 203 has not been selected, i.e. when the "Cancel" button 204 is selected (S8:NO), the processing returns to S2.

If the "OK" button 203 is selected (S8:YES), the CPU 21 analyzes the QR code and extracts the folder generating information (S9). The S9 processing configures an analyzing portion for analyzing the image obtained by image-picking up with the image pickup unit 41, which is an image pickup portion, and extracting folder generating information in the folder generating mode for extracting the folder generating information on generation of a plurality of folders recording a plurality of image data of the inspection object.

Then, the CPU 21 creates a plurality of folders in the memory card 11, based on the folder generating information (S10). The S10 processing configures a folder generating portion for generating a plurality of folders on the inspection object, based on the folder generating information extracted in the processing of S9, which is an analyzing portion. Successively, the CPU 41 deletes the image data of the QR code in RAM 23 if the image of the QR code is stored in the RAM 23 (S11).

As above, it is possible to generate the folder of the inspection object by reading the two-dimensional code attached to the housing OB etc. of the inspection object by a sticker etc., using the endoscope system.

Besides, if the input operation mode is not the folder generating mode (S1: NO), the CPU 21 transfers to processing in an endoscope inspection mode (S12).

Incidentally, in the above example, if the QR code is correctly read and the QR code is a QR code for generating a folder, the screen of a confirmation message is displayed on the screen 4a of the LCD 4 for user's confirmation. However, a plurality of folders may be generated without user's confirmation, i.e. without performing processing of S6 and S8.

(Folder Configuration)

The folder configuration generated by generation processing of a folder will be described.

As described above, the user images the QR code attached to the inspection object with the image pickup unit 41 in the inserting portion 7 of the endoscope system 1. Then, a plurality of folders having a hierarchical structure on the inspection object are generated in the memory card 11, at the inspection site prior to endoscope inspection. A folder name is assigned to each of the generated folders. Therefore, folder generating information includes folder names for a plurality of folders to be generated.

And then, as described later, in the endoscope inspection mode, the user may record the endoscope image obtained by image-picking up with the image pickup unit 41 of the scope unit 3 in a desired folder of the plurality of folders having a hierarchical structure.

Figure 9:
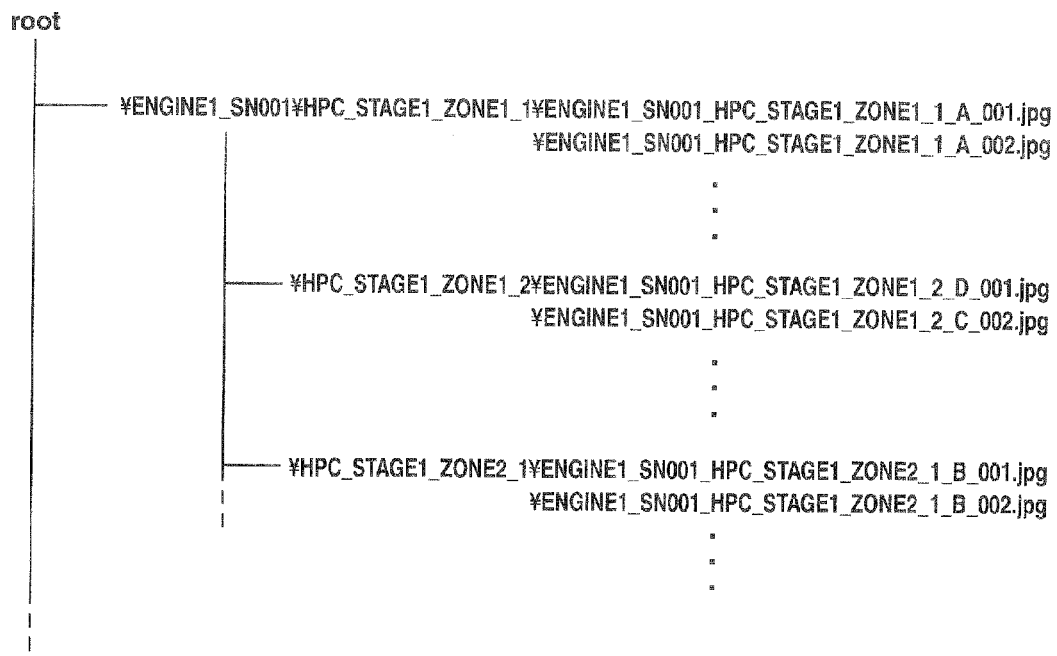
FIG. 9 is a diagram for explaining an example of a folder having a hierarchical structure in accordance with the embodiment of the present invention.

FIG. 9 is a diagram for explaining an example of a folder having a hierarchical structure. Incidentally, FIG. 9 represents each folder and files included in that folder schematically in order to describe the folder having a hierarchical structure, here indicating an example where the folder has two hierarchies, i.e. two levels.

As shown in FIG. 9, the folder "ENGINE1_SN001" is created under "root", and a plurality of lower folders are included under the folder "ENGINE1_SN001".

In FIG. 9, three lower folders are shown: "HPC_STAGE1_ZONE1_1", "HPC_STAGE1_ZONE1_2" and "HPC_STAGE1_ZONE2_1".

"ENGINE1" in "ENGINE1_SN001" is, for example, an engine name, and "SN001" is a serial number, etc. In an embodiment of the invention, "ENGINE1_SN001", which is a combination of an engine name and a serial number, is the inspection target information.

The folder "ENGINE1_SN001" and a group of folders "HPC_STAGE1_ZONE1_1", "HPC_STAGE1_ZONE1_2" and "HPC_STAGE1_ZONE2_1" are mutually in different hierarchies.

In other words, a folder for the inspection object as shown in FIG. 9 is generated automatically under "root" in the memory card 11 by generation processing of a folder as described above. Then, as described later, the user selects any folder out of the plurality of folders generated in advance in this way as the recording destination folder of the endoscope image. Then, the user may record the endoscope image in the selected folder.

Incidentally, although the hierarchies of folders generated based on the QR code are of two in the embodiment of the present invention, there may be three or more hierarchies of folders. Further, as shown in dotted lines in FIG. 9, the number of folders in the same hierarchy may also be three or more. Besides, the hierarchy of folders does not need to be necessarily two or more, but the folder structure may have only one hierarchy under "root".

As shown in FIG. 9, it is indicated that a plurality of endoscope images in the JPEG format are recorded in three lower folders of "HPC_STAGE1_ZONE1_1", "HPC_STAGE1_ZONE1_2" and "HPC_STAGE1_ZONE2_1".

The file name included in each folder is of structure with a file mark and a serial number added to the folder name of upper and lower hierarchies. In other words, the file name is "Upper folder's name_Lower folder's name_File mark_Serial number.jpg".

For example, the folder name "ENGINE1_SN001" of the upper folder and the folder name "HPC_STAGE1_ZONE1_1" of the lower folder are connected with the mark "_" (underscore) and the file mark "A" and the serial number "001" are further added to generate the file name of "ENGINE1_SN001_HPC_STAGE1_ZONE1_1_A_001.jpg". The structure of a file name will be further described later.

Figure 10:
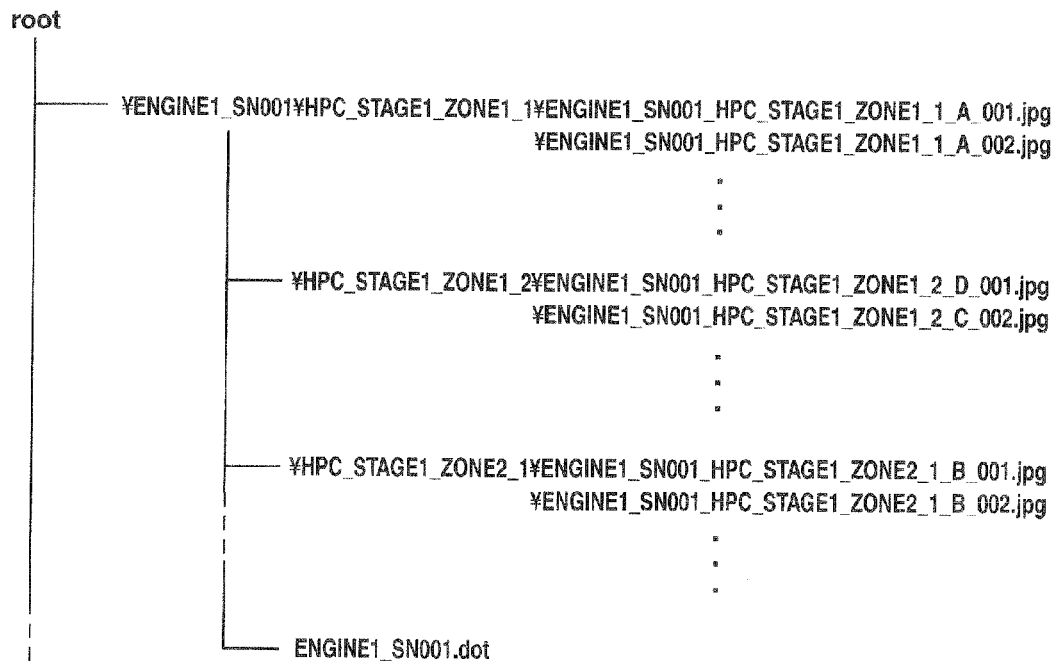
FIG. 10 is a diagram for explaining an example of the hierarchical structure of a folder if report template information of an endoscope inspection report is included in accordance with the embodiment of the present invention.

Incidentally, template information of an endoscope inspection report (hereinafter also referred to simply as report) may be included in the QR code, which is inspection object identifying information. FIG. 10 is a diagram for explaining an example of the hierarchical structure of a folder if report template information of an endoscope inspection report is included. In FIG. 10, the report template information of "ENGINE1_SN001.dot" is included as information of one file in the folder. In this way, report template information for generating a report is so arranged as to be included in the QR code, which is inspection object identifying information, in addition to information of the folder structure for storing image data of an endoscope image.

The report template information for generating a report is read together with folder information (including the template information) when the QR code is read in the above generation processing of a folder. Then, the read report template information is temporarily stored in the RAM 23 together with the folder information. Further, the report template information is transmitted to and stored in the memory card 11 as one file.

(Image Recording and Screen Display)

Figure 11:
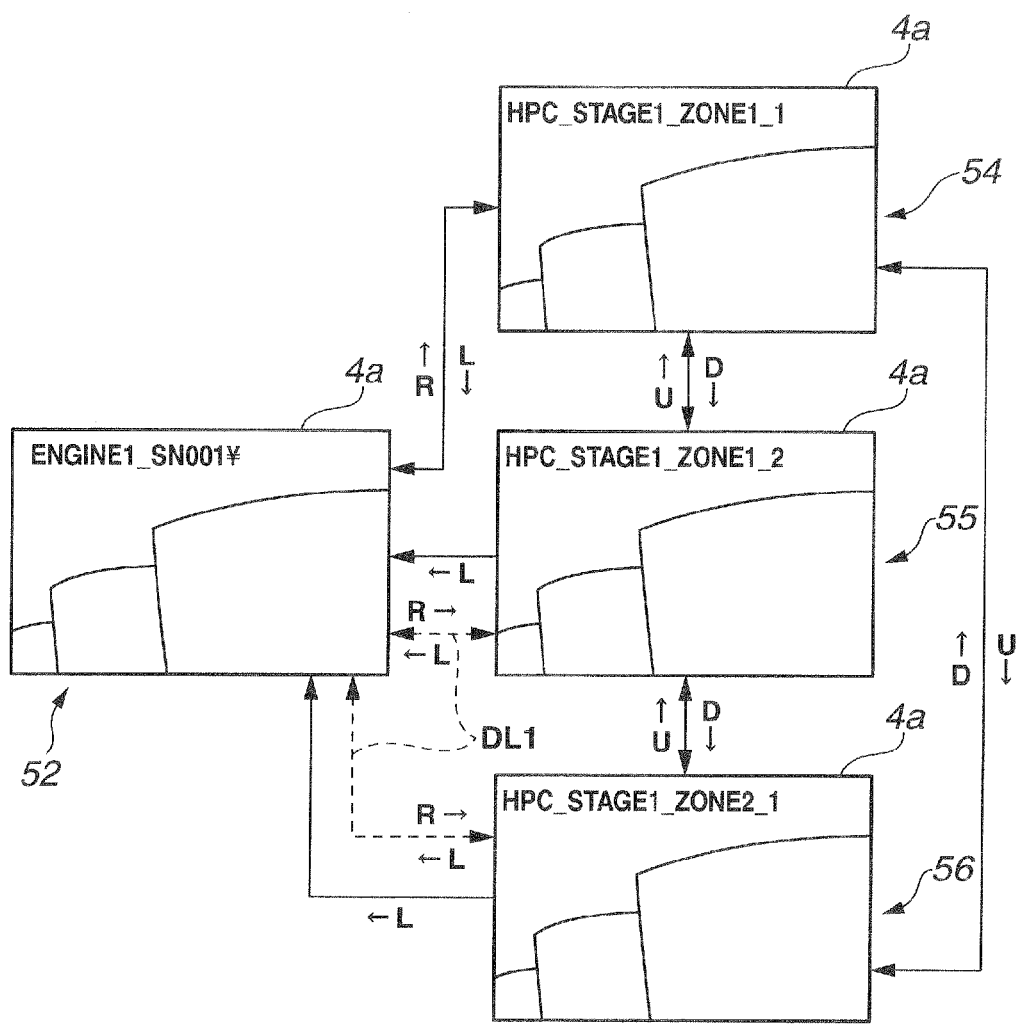
FIG. 11 is a diagram for explaining transition of screen display during change of a recording destination folder in accordance with the embodiment of the present invention.

Next, the screen display will be described during change of the recording destination folder of the endoscope image obtained by image-picking up when the endoscope system 1 is set to the endoscope inspection mode. FIG. 11 is a diagram for explaining transition of screen display during change of a recording destination folder.

When the power supply of the endoscope system 1 is turned ON, a live image of the object being photographed with the image pick up unit 41 is usually displayed on the screen of the LCD 4. The user performs inspection while viewing the live image of the inspection object (a turbine blade in FIG. 11) displayed on the screen.

On the screen 4a of the LCD 4, the live image and the recording destination folder name of the image is displayed. After the power supply is turned ON, "ENGINE1_SN001¥" under "root" is displayed on the screen 4a as the recording destination folder.

Incidentally, although the information "ENGINE1_SN001¥" indicating that the recording destination folder is the folder of "ENGINE1_SN001" is displayed on the upper left of the screen 4a in the screen 52 of FIG. 11, its location of the information may not necessarily be on the upper left of the screen but may be, for example, on the upper right.

Still further, in case of FIG. 11, although a mark "¥" is added to the folder name of the recording destination folder as the information indicating the recording destination folder on the screen 52, the mark "¥" does not need to be present.

Additionally, in the case of FIG. 11, although the information indicating the recording destination folder is the information that includes the folder name of the recording destination folder, the user has to only be able to recognize and identify the recording destination folder. Therefore, the information indicating the recording destination folder does not have to include all of the recording destination folder names but may be, for example, the one including only the folder name of the hierarchy selected currently.

If the user wants to record a still image in a desired folder generated in advance, it is possible to select the folder in the state of the live image being displayed on the LCD 4 by operating the joystick 5b. If the joystick 5b is inclined in either direction of upper (U), lower (D), left (L) or right (R), a folder is selected out of the plurality of folders each having a hierarchical structure according to the direction and is set as the recording destination folder.

In FIG. 11, three folders have been created under the folder "ENGINE1_SN001" as shown in FIG. 9, and screen transition in case of selecting a recording destination folder from the group of these folders is displayed. The sequence of displaying recording destination folders in each hierarchy has been set in advance so as to be performed in a predetermined sequence such as the date of folder creation and the alphabetical order of folder names.

As shown in FIG. 11, if the joystick 5b is inclined downwards (i.e. inclined in the D direction) from the state of the screen 52, the screen does not change because there is no other folder in the same hierarchy.

Even if the joystick 5b is inclined upwards (i.e. inclined in the U direction) in the state of the screen 52, the screen does not change because there is no other folder in the same hierarchy.

Further, if the joystick 5*b* is inclined to the right (i.e. inclined in the R direction) in the state of the screen 52, the folder "HPC_STAGE1_ZONE1_1", which is the first folder in the lower hierarchy (the uppermost folder in FIG. 9), is selected as the recording destination folder, and the screen 52 changes to the screen 54.

Still further, if the joystick 5*b* is inclined to the left (i.e. inclined in the L direction) in the state of the screen 54, the folder "ENGINE1_SN001", which is a folder in the upper hierarchy, is selected as the recording destination folder and the screen 54 changes to the screen 52.

If the joystick 5*b* is inclined downwards (i.e. inclined in the D direction) from the state of the screen 54, the folder "HPC_STAGE1_ZONE1_2", which is the next folder in the same hierarchy, is selected as the recording destination folder and the screen 54 changes to the screen 55.

If the joystick 5*b* is inclined upwards (i.e. inclined in the U direction) in the state of the screen 55, the folder "HPC_STAGE1_ZONE1_1", which is the previous folder in the same hierarchy, is selected as the recording destination folder and the screen 55 changes to the screen 54.

If the joystick 5*b* is inclined downwards (i.e. inclined in the D direction) from the state of the screen 55, the folder "HPC_STAGE1_ZONE2_1", which is the next folder in the same hierarchy, is selected as the recording destination folder and the screen 55 changes to the screen 56.

Further, if the joystick 5*b* is inclined upwards (i.e. inclined in the U direction) in the state of the screen 54, the folder "HPC_STAGE1_ZONE2_1", which is the last folder in the same hierarchy, is selected as the recording destination folder and the screen 54 changes to the screen 56.

Further, if the joystick 5*b* is inclined downwards (i.e. inclined in the D direction) in the state of the screen 56, the folder "HPC_STAGE1_ZONE1_1", which is the first folder in the same hierarchy, is selected as the recording destination folder and the screen 56 changes to the screen 54.

Still further, if the joystick 5*b* is inclined to the left (i.e. inclined in the L direction) in the states of either the screen 55 or the screen 56, the folder "ENGINE1_SN001", which is a folder in the upper hierarchy, is selected as the recording destination folder and the screens 55 or 56 changes 56 to the screen 52.

Therefore, the user may confirm the recording destination folder while viewing the live image and easily change the recording destination folder. As above, the LCD 4 configures a display portion for displaying one folder out of a plurality of folders in the endoscope inspection mode. And then, the joystick 5*b* configures an operation unit for changing one folder being displayed on the LCD 4 as a display portion to another folder in the endoscope inspection mode.

Additionally, in case of FIG. 11, if the joystick 5*b* is inclined to the right (i.e. inclined in the R direction) in the state of the screen 52 after the screen has changed from the screens 55 or 56 to 52, the screen 52 changes to the screen 54 so that the folder "HPC_STAGE1_ZONE1_1", which is the first folder in the lower hierarchy, may be selected as the recording destination folder. However, if the joystick 5*b* is inclined to the right (i.e. inclined in the R direction) in the state of the screen 52 after the screen has changed from the screens 55 or 56 to 52, it may be arranged that the screen 55 or 56 is displayed as shown in dotted lines DL1 in FIG. 11. For this purpose, the folder data of the transition screen is kept stored in the RAM 23 and the CPU 21 controls the screen display so that the changed previous folder may be displayed.

In the embodiment of the present invention, although only the folder name in the hierarchy being selected currently is displayed, the folder name in the folder's upper hierarchy may be displayed together when, for example, the CPU 21 displays a folder name in the lower hierarchy. At this time, the folder name on the screen 54 is made, for example, "ENGINE1_SN001¥HPC_STAGE1_ZONE1_1".

(Changing Processing of Recording Destination Folder)

Figure 12:
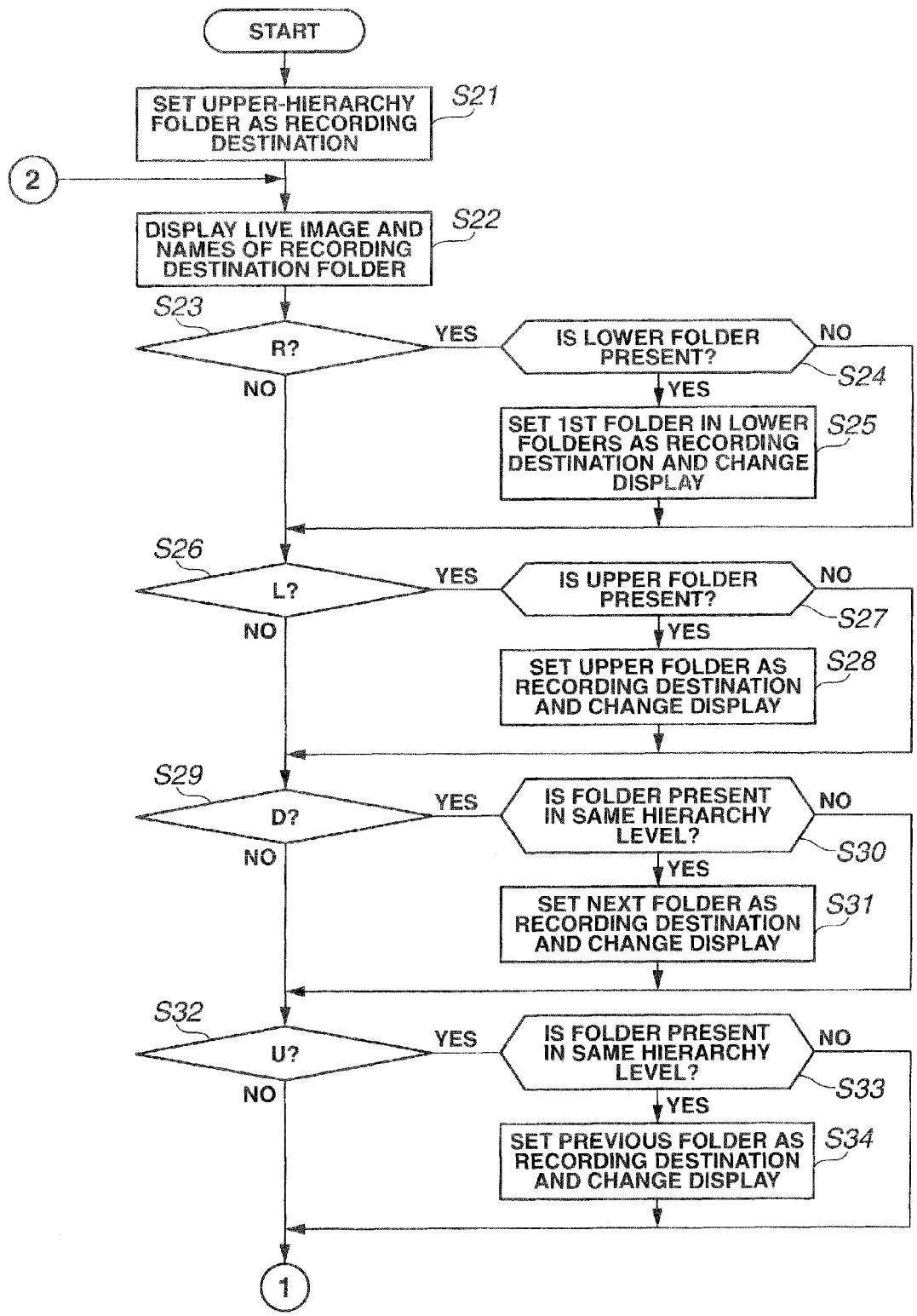
FIG. 12 is a flowchart illustrating an example of flow of changing processing of a recording destination folder in accordance with the embodiment of the present invention.
Figure 13:
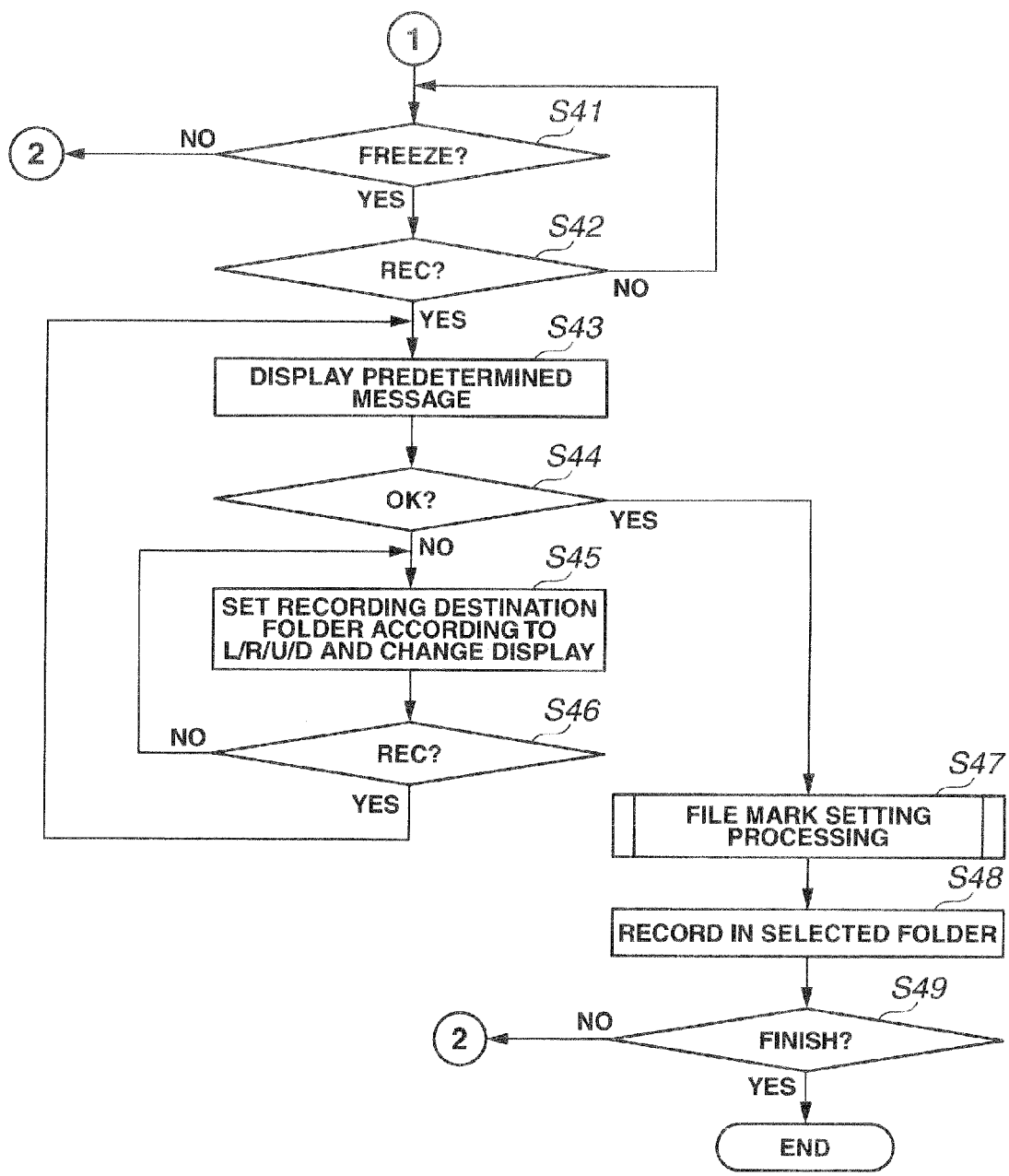
FIG. 13 is a flowchart illustrating an example of flow of changing processing of a recording destination folder in accordance with the embodiment of the present invention.

Next, the changing processing of the above described recording destination folder will be described. FIGS. 12 and 13 are flowcharts each indicating an example of flow of changing processing of the recording destination folder.

First, when the power supply of the endoscope system 1 is turned ON, the CPU 21 sets the folder "ENGINE1_SN001", which is a folder in the upper hierarchy, as the recording destination folder after various kinds of initial processing have been executed (S21). Its setting data are stored, for example, in a predetermined storage area of the RAM 23 as setting data of the recording destination folder in image recording processing that the endoscope system 1 has.

Thereafter, the CPU 21 displays the live image and the name of the recording destination folder on the screen 4*a* of the LCD 4 as shown on the screen 52, based on imaging signals from the image pickup unit 41 (S22). The S22 processing configures a recording destination folder information display portion for displaying the information indicating the recording destination folder in a state where the endoscope image is displayed in the display portion.

Next, the CPU 21 determines whether the joystick 5*b* has been inclined in the right (R) direction or not (S23), and determines whether there is a lower folder for the current recording destination folder or not (S24) when the joystick 5*b* is inclined in the right (R) direction (S23:YES).

If there is no lower folder (S24:NO), the processing proceeds to S26. If there is a lower folder (S24:YES), the CPU 21 sets the first folder of the lower folders as the recording destination folder, changing display of the recording destination folder name in the screen 4*a* (S25). Because the information of the recording destination folder is stored in the predetermined storage area of the RAM 23 as described above, the data in the predetermined storage area are rewritten by the setting, i.e. changed folder's data.

For example, if the joystick 5*b* is inclined in the right (R) direction in a state where the folder "ENGINE1_SN001" is the recording destination folder (the screen 52), the folder "HPC_STAGE1_ZONE1_1", which is the first folder in the lower hierarchy, is set as the recording destination folder. In other words, the screen 52 changes to the screen 54.

In the case of NO in S23, NO in S24 and after S25 processing, the CPU 21 determines whether the joystick 5*b* has been inclined in the left (L) direction or not (S26), and determines whether there is an upper folder of the current recording destination folder or not (S27) when the joystick 5*b* is inclined in the left (L) direction (S26:YES).

If there is no upper folder (S27:NO), the processing proceeds to S29. If there is an upper folder of the current recording destination folder (S27:YES), the CPU 21 sets the upper folder as the recording destination folder, changing display of the recording destination folder's name in the screen 4*a* (S28).

Incidentally, because there is no upper folder for the folder "ENGINE1_SN001", the CPU 21 determines that there is no upper folder even if the joystick 5*b* is inclined in the left (L) direction in the state of the screen 52 (S27:NO). Therefore, in this case, the screen 52 does not change.

In case of NO in S26, NO in S27 and after the S28 processing, the CPU 21 determines whether the joystick 5*b* has been inclined downwards (D) or not (S29), and determines whether there is a folder in the same hierarchy as the current recording destination folder or not (S30) when the joystick 5b is inclined downwards (D) (S29:YES).

If there is no folder in the same hierarchy (S30:NO), the processing proceeds to S32. If there is a folder in the same hierarchy as the current recording destination folder (S30: YES), the CPU 21 sets the next folder in the same hierarchy as the recording destination folder, changing display of the recording destination folder's name in the screen 4a (S31).

For example, if the joystick 5b is inclined downwards (D) in the state of the screen 54 that the folder "HPC_STAGE1_ZONE1_1" is set as the recording destination folder, the screen 54 changes to the screen 55 where the folder "HPC_STAGE1_ZONE1_2" is set as the recording destination folder. Further, if the joystick 5b is inclined downwards (D) in the state of the screen 55, the screen 55 changes to the screen 56 where the folder "HPC_STAGE1_ZONE2_1" is set as the recording destination folder. Further, if the joystick 5b is inclined downwards (D) in the state of the screen 56, the folder "HPC_STAGE1_ZONE1_1" is set as the recording destination folder, which is the first folder in the same hierarchy, because there is no next folder in the same hierarchy. In other words, the screen 56 changes to the screen 54.

In the case of NO in S29, NO in S30 and after S31 processing, the CPU 21 determines whether the joystick 5b has been inclined upwards (U) or not (S22), and determines whether there is a folder in the same hierarchy as the current recording destination folder or not (S33) when the joystick 5b is inclined upwards (U) (S32:YES).

If there is no folder in the same hierarchy (S33:NO), the processing proceeds to S41. If there is a folder in the same hierarchy as the current recording destination folder (S33: YES), the CPU 21 sets the previous folder in the same hierarchy as the recording destination folder, changing display of the recording destination folder's name in the screen 4a (S34).

For example, if the joystick 5b is inclined upwards (U) in the state of the screen 55 that the folder "HPC_STAGE1_ZONE1_2" is set as the recording destination folder, the screen 55 changes to the screen 54 where the folder "HPC_STAGE1_ZONE1_1" is set as the recording destination folder. Further, if the joystick 5b is inclined upwards (U) in the state of the screen 54, the folder "HPC_STAGE1_ZONE2_1", which is the last folder in the same hierarchy, is set as the recording destination folder because there is no previous folder in the same hierarchy. In other words, the screen 54 changes to the screen 56.

The above described processing from S23 to S34 configures a recording destination folder changing portion for changing a recording destination folder according to operation of the operation unit 5. Concretely, the processing from S23 to S34 configures the recording destination folder changing portion for changing the recording destination folder in a state where a live image is displayed.

Returning to FIG. 12, in the case of NO in S32, NO in S33 and after S34 processing, the CPU 21 determines whether the freeze button has been pressed or not (S41 in FIG. 13).

If the freeze button is not pressed (S41:NO), the processing returns to S22. If the freeze button is pressed (S41:YES), the CPU 21 determines whether the REC button has been pressed or not (S42). The REC button is a button for giving an instruction to record a frozen image in a recording medium. Incidentally, when the freeze button is pressed, the CPU 21 generates and displays a still image on the LCD 4, based on the imaging signal from the image pickup unit 41.

Besides, the structure may be made so that the recording destination folder can be changed in the frozen state of the live image when the freeze button is pressed in S41, the same as S23 to S34 in a state where the live image is displayed.

If the REC button is not pressed, the processing returns to S41 and whether the frozen state is continued, in other words, whether the frozen state has not been cancelled or not is determined. If the frozen state has been cancelled (S41:NO), the processing returns to S22.

Figure 14:
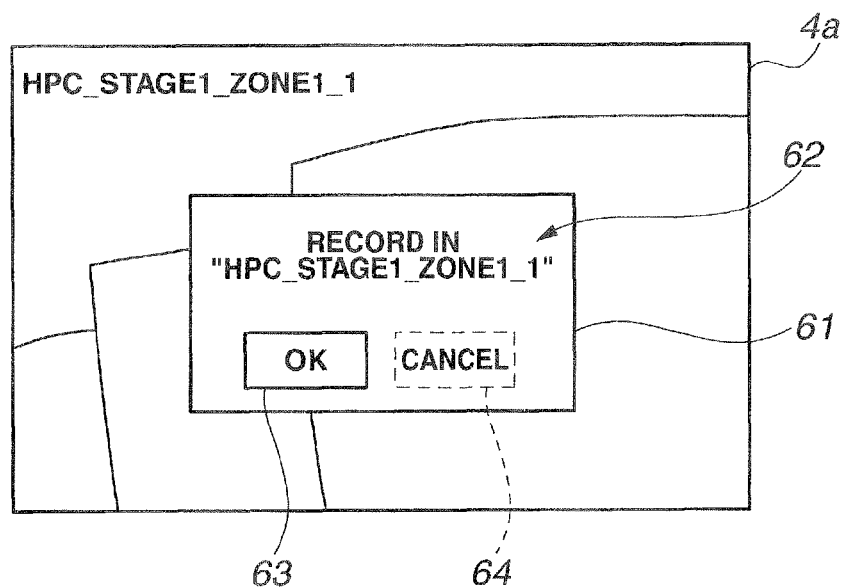
FIG. 14 is a diagram indicating a display example of a confirmation message in accordance with the embodiment of the present invention.

If the REC button is pressed (S42:YES), the CPU 21 displays the predetermined confirmation message as shown in FIG. 14 on the screen 4a (S43).

FIG. 14 is a diagram indicating a display example of the confirmation message. On the screen 4a of the LCD 4, a still image by freezing is displayed, and on the screen of the still image a predetermined confirmation message is displayed in a window 61. FIG. 14 is a display example if the REC button is pressed in the state of the screen 54, where the message 62 reading "Recording in HPC_STAGE1_ZONE1_1" is being displayed in the window 61.

Further, the window 61 includes an "OK" button 63 and a "Cancel" button 64. The user may select the "OK" button 63 or the "Cancel" button 64 by performing a predetermined operation at the operation unit 5. Incidentally, because the "OK" button 63 is in the selected state by default in FIG. 14, the "OK" button 63 is displayed more highlightedly than the "Cancel" button 64.

The user selects the "OK" button 63 if the still image obtained by freezing is to be recorded in the folder shown in the confirmation message. On the other hand, the user selects the "Cancel" button 64 if the still image obtained by freezing is to be recorded in any other folder than shown in the confirmation message.

After S43, the CPU 21 determines whether the "OK" button 63 has been pressed or not, and if the "OK" button 63 is not pressed, i.e. if the "Cancel" button 64 has been pressed (S44:YES), the CPU 21 deletes the window 61 from on the screen 4a, and the processing transfers to S45.

On the screen 4a, the still image by freezing and the name of the currently set recording destination folder are indicated. The user may change the recording destination folder by operating the joystick 5b in the displayed state of that screen.

Figure 15:
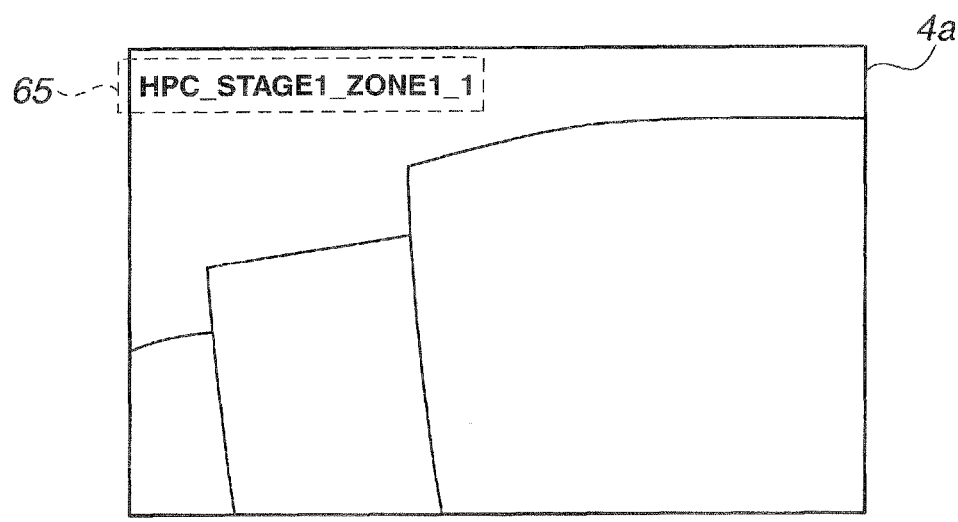
FIG. 15 is a diagram indicating an example of screen of a case where a recording destination folder is changed in a state where a still image is displayed in accordance with the embodiment of the present invention.

FIG. 15 is a diagram indicating an example of screen of a case where a recording destination folder is changed in a state where a still image is displayed. When the joystick 5b is operated in a state where a still image displayed by freezing is kept displayed, the recording destination folder is changed according to the operation. Then, on the screen 4a, only the folder name to be displayed in the recording destination folder displaying area 65 for displaying a recording destination folder changes according to operation of the joystick 5b. Therefore, the user may change the recording destination folder by operating the joystick 5b to display the desired recording destination folder name on the recording destination folder displaying area 65.

The processing S45 configures a recording destination folder changing portion for changing a recording destination folder according to operation of the operation unit 5 and at the same time, configures a recording destination folder information display portion for displaying the information indicating a recording destination folder in a state where an endoscope image is displayed on the LCD 4.

In particular, the S45 processing configures a recording destination folder changing portion capable of changing a recording destination folder in a state where an endoscope image is displayed on the LCD 4.

As above, in the case of NO in S44, the recording destination folder is changed in the CPU 21 as shown in FIG. 11 according to the inclination operation in U/D/L/R directions of the joystick 5b, and the user selects a desired folder as the recording destination folder, thus changing display of the recording destination folder's name in the screen 4a (S45).

The CPU 21 determines again in a state where the recording destination folder is changed whether the REC button has been pressed (S46). If the REC button is not pressed (S46: NO), the processing returns to S45.

If the REC button is pressed in S46 (S46:YES), the processing transfers to S43, and the CPU 21 displays a predetermined message for confirming the recording destination folder (S43).

When the recording destination folder is confirmed (S44: YES), the setting processing of a file mark is executed (S47). The file mark is a predetermined mark functioning as an identification mark to be added to the file name to be recorded.

The file mark is to be added optionally by the user to indicate what kind of image is the recorded image. For example, in order to classify images into "No problem (Accept)", "Replacement required (Reject)", "Repair required (Repair)" and "Reinspection required (Re-Inspect)", a file mark is added to each file name. In other words, the file mark is the inspection result information that the user as an inspector gives to an endoscope image upon viewing the endoscope image. Moreover, there is a classification of "None". "None" means that there is no file mark (i.e. a file mark cannot be attached). Therefore, addition of file marks is an option of the user.

Figures 16, 17:
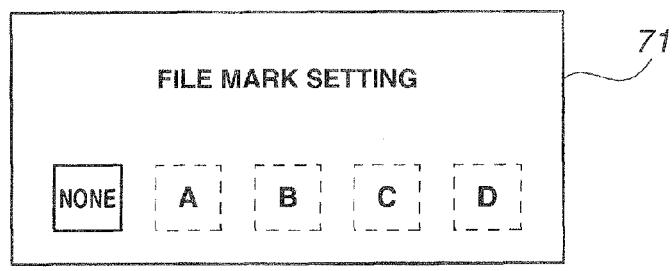
FIG. 16 is a diagram indicating a display example of a file mark setting window in file mark setting processing in accordance with the embodiment of the present invention.
FIG. 17 is a diagram for explaining a file name structure in accordance with the embodiment of the present invention.

FIG. 16 is a diagram indicating a display example of a file mark setting window in file mark setting processing.

The window 71 of FIG. 16 is also displayed as a pop-up window on the still image displaying screen like the window 61. The user may select any one of four kinds (five kinds if "None" meaning no addition is included) by performing a predetermined operation in the operation unit 5. In case of FIG. 16, it is possible to add four kinds of file marks, "A", "B", "C" and "D". Here, "A" corresponds to "No problem (Accept)", "B" to "Replacement required (Reject)", "C" to "Repair required (Repair)" and "D" to "Reinspection required (Re-Inspect)".

Incidentally, although the file mark is a single character here, a plurality of characters or a character string such as "ACCEPT" or "REPAIR" may also be used.

The file name is a folder name of the folder to be recorded with a file mark and a serial number added. Therefore, the user may recognize the inspection result on the endoscope image in the file merely by viewing the file mark in the file name. For example, if the file name is "HPC_STAGE1_ZONE1_1_A_001.jpg", its file mark is "A", and therefore, it is obvious that the inspection result is "No problem (Accept)". If the fine name is "HPC_STAGE1_ZONE1_1_B_001.jpg", its file mark is "B", and therefore, it is obvious that the inspection result is "Replacement required (Reject)".

Therefore, the user may judge the inspection region etc. from the file name and also the kind of image.

Incidentally, FIG. 16 indicates the state that "None" meaning no addition has been selected by default when the window 71 is displayed. Therefore, if the operation instructing decision of selection is performed in the state of FIG. 16, a file mark is not given to the file name. In other words, the file name is set to be "HPC_STAGE1_ZONE1_1_001.jpg" etc.

The processing S47 configures an identification mark setting portion for selecting and setting a file mark from a predetermined plurality of file marks.

Returning to FIG. 13, in the case of YES in S44, the processing moves to file mark setting processing (S47), and the file mark adding processing is executed for adding a file mark to the file name as described above.

Thereafter, the CPU 21 records the image in the recording destination folder selected or set (S48). In S48, the endoscope image is recorded in the recording destination folder set as the recording destination of the endoscope image out of a plurality of folders created in advance in the memory card 11. In other words, the S48 processing configures an inspected image recording portion for recording each image data of the inspection object obtained by image-picking up with the image pickup unit 41, which is an image pickup portion, in one folder out of a plurality of folders generated by the folder generating portion, in the endoscope inspection mode for recording a plurality of image data of the inspection object.

Further, in S48, if a still image of the endoscope image obtained in response to the instruction for recording from the operation unit 5 is recorded, the CPU 21 displays a predetermined message on the recording destination folder. After the confirmation message is displayed, the still image is recorded in the recording destination folder set or changed.

Still further, in S48, the file mark set in S47 is added to the file name of the endoscope image, thus the endoscope image being recorded in the recording destination folder.

Then, the CPU 21 determines whether finish has been instructed or not (S49); if the finish is instructed (S49:YES), the processing is finished, and if the finish is not instructed (S49:NO), the processing moves to S22.

Further, in the above described embodiment, the joystick is an operation unit operable in the first left-and-right direction and in the second up-and-down direction which is orthogonal to the left-and-right direction, and change of the recording destination folder comprises: changing the recording destination folder by hierarchical transition in the up-and-down direction of the hierarchical structure in response to the operation in the left-and-right direction; and changing the recording destination folder by transfer within the same hierarchy of the hierarchical structure in response to the operation in the up-and-down direction. Therefore, good operability is provided because the user is capable of changing the screen by operation of the joystick corresponding to the image of the folder's hierarchical structure.

Still further, the operation unit for changing a recording destination folder may be a so-called cross-key, a U/D/L/R key, a button to which a function is assigned during folder change, or the like in place of the joystick. Besides, the operation unit may be a cross-key, a U/D/L/R key, or the like generated by software and displayed on the screen.

Further, although the joystick 5b is an exclusive joystick for changing or selecting a recording destination folder in the above described embodiment, an up/down/left/right (U/D/L/R) bending button 5a being used for bending operation may be used as an actuator for selecting a recording destination folder under switchover of modes.

Still further, although information indicating a recording destination folder is displayed when a live image is displayed in the above described embodiment, the information for indicating a recording destination folder may be so arranged as to be displayed only when the freeze button is pressed.

As shown in FIG. 11, the user may confirm the recording destination folder when an endoscope image is recorded and change the recording destination folder easily.

Further, on the screens as shown in FIGS. 11, 14, 15, etc., the folder name is indicated, but in the embodiment of the present invention, because the character string for the purpose of inspection in the folder name is composed of numerals, there may be a case where the user wants to confirm the meaning of those numerals. Thereupon, it may be arranged that when the user places the cursor on the character string indicating the purpose of inspection or performs a predetermined operation in the displayed state of, for example, the screen in FIG. 11 etc., the contents meant by those numerals is displayed in the window. For example, when the cursor is moved to the position of the lowermost "1" of the folder name "HPC_STAGE1_ZONE1_1" in FIG. 14, the character string "Cracks" is displayed. Therefore, it becomes possible for the user as an inspector to confirm the purpose of the current inspection or easily confirm whether the folder in the storage destination is a folder in a correct storage destination.

(Structure of File Name)

Here, the file name structure will be described. FIG. 17 is a diagram for explaining a file name structure. The file name consists of five elements of the first to five portions, 81 to 85. Each element is separated by a predetermined mark in between.

An example of the file name in FIG. 17 is "ENGINE1_SN001_HPC_STAGE1_ZONE1_1_A_001.jpg". The first "ENGINE1_SN001" in this file name is the folder name portion 81 in the first hierarchy, for example, inspection target information consisting of the character string indicating an inspection object shown by an engine name and a serial number.

The next "HPC_STAGE1_ZONE1_1" is the folder name portion 82 in the second hierarchy, which is lower than the first hierarchy, for example, inspection location information and inspection purpose information consisting of the character string indicating an inspection location (or a region) and an inspection purpose. "HPC_STAGE1_ZONE1" is the inspection location information indicating the inspection region or location. The last "1" separated from "HPC_STAGE1_ZONE1" with the mark "_" (underscore) is the inspection purpose information, which is a character string (shown here is a numeral) indicating an inspection purpose, i.e. what will be inspected, for example, a crack will be inspected or a surface defect will be inspected. In the embodiment, if the last character (numeral) of the folder name portion 82 is "1", it means a crack inspection; "2" indicates a surface defect (peeling-off etc.) inspection; and "3" indicates a corrosion inspection. In other words, the last character of the folder name portion 82 is inspection purpose information.

As above, the first portion 81 and the second portion 82 are those that include the folder name of the folder where the relevant file is recorded. Also, because the folder name includes the information on the inspection object, the inspection region and the inspection purpose, a plurality of files of endoscope images will be stored separately for each inspection purpose. In other words, the folder structure indicates the contents or procedure of inspection.

Additionally, "A" in the file name is the file mark portion 83. The file mark is inspection result information consisting of a character indicating the inspection result. The inspection result information is information of the determined result that the user has determined in the endoscope inspection. For example, if the file mark in the file name is "A", it means that its endoscope image has been judged "No problem" by the user because the component subject to inspection does not have a crack. If the file mark in the file name is "B", it means that its endoscope image has been judged "Replacement required" by the user because the component has a crack. If the file mark in the file name is "C", it means that its endoscope image has been judged "Repair required" by the user because the component has a crack. If the file mark in the file name is "D", it means that its endoscope image has been judged "Reinspection required" by the user because the component has a crack.

Further, "001" in the file name is the serial number portion 84. When an endoscope image is recorded in the folder for the first time, the serial number portion 84 is made "001", and the serial number is identifying information being incremented by "1" every time when an endoscope image is added thereafter.

The "jpg" in the file name is the extension portion 85 being the character string for identifying the kind of file.

As above, the inspection target information, the inspection location information, the inspection purpose information, the inspection result information and the serial number corresponding to each of the first to fourth portions 81 to 84 included in the file name are mutually separated using a predetermined mark (here, "_" [underscore]).

Incidentally, although each of the first to fourth portions 81 to 84 is separated here by "_" (underscore), any other mark such as "-" (hyphen), "/" (slash) or any particular character may be used for separation.

Incidentally, the mark "_" (underscore), which is the same as the separating mark, is used in the portions 81 and 82, but because the structure of the character string in each portion has been decided in advance, the PC 43 is capable of identifying and extracting each element in the file name when a report is generated, based on the predetermined component information for each portion, as described later.

As above, an endoscope image is recorded in the folder selected by the user, and a folder name and a file mark are included in the file name of each endoscope image in each folder.

As above, according to the embodiment of the present invention, it is possible to generate suitably a plurality of suitable folders for storing the endoscope image obtained by image pickup of a code such as the QR code with the endoscope system according to the inspection object in an endoscope inspection.

Incidentally, as described above, report template information may be included in the QR code as shown in FIG. 10. Hereafter, report generation in a case where report template information is included in the QR code will be described.

Up to the present, a proposal exists for the technology capable of making an output screen composition in a free layout if information such as a picture or a text stored in a database is output by means of displaying or printing, for example, as disclosed in Japanese Patent Application Laid-Open Publication No. 2006-276991.

The report on a plurality of endoscope images obtained by the endoscope system must be generated properly in a corresponding format for each inspection object. However, the method of properly generating a report with a plurality of endoscope images obtained in inspection attached in accordance with a template corresponding to the inspection object has not been disclosed in the above proposal.

Therefore, it is made possible here to generate a report properly with a plurality of endoscope images obtained in inspection attached, by including report template information in a QR code and using such template information.

Since report template information is included in the QR code, the information is extracted in the S9 analyzing processing in FIG. 4 as described above. In other words, the QR code, which is inspection object identifying information, includes report template information, and in the S9 processing, the image obtained by image-picking up with the image pickup unit 41, which is an image pickup portion, is analyzed, thus report template information being extracted. Therefore, the S9 processing configures a report template information extracting portion.

(Composition of Endoscope Inspection Report)

First, the composition of a report to be generated based on the report template information included in the QR code will be described.

FIG. 18 is a diagram for explaining an example of the composition of an endoscope inspection report. An endoscope inspection report 100 is screen-displayed or printed, and FIG. 18 indicates the composition of a report when screen-displayed or printed. The report 100 in the embodiment of the present invention is in a tabular format, being composed of five sections: a section 101 for the upper inspection location (Area), a section 102 for the lower inspection location (Block Location), a section 103 for the inspection purpose (Reason for Inspection), a section 104 for the inspection result (Outcome) and a section 105 for the endoscope image (Picture). The report 100 further has a title portion 106 displaying the inspection object.

The report 100 is generated with the file name information. In the title portion 106 "ENGINE1_SN001" is shown, indicating that the report is on the inspection object "ENGINE1_SN001". This title portion 106 corresponds to the character string of the first portion 81 of the file name.

In an example of FIG. 18, "HPC" is shown in the section 101, indicating that the inspection location is "HPC". This section 101 corresponds to the character string in the former part of the second portion 82 of the file name.

In the section 102 "STAGE1_ZONE1" etc. is shown, indicating that the inspection location is "STAGE1_ZONE1" etc. This section 102 corresponds to the character string in the middle of the second portion 82 of the file name.

"Cracks" etc. is shown in the section 103, indicating that the inspection purpose is the inspection etc. of "Cracks", i.e. a crack. This section 103 corresponds to the character string in the latter part of the second portion 82 of the file name.

Incidentally, as described later, the character strings shown in the sections 101 to 103 have been registered in advance in the predetermined template prepared in advance for each inspection object.

In the section 104, "Accept" etc. is shown, indicating that the inspection result is "Accept (No problem)" etc. This section 104 is generated based on the character string in the third portion 83 of the file name.

An endoscope image corresponding to the file name is attached to the section 105.

In FIG. 18, as an example, an endoscope image 111 judged "Accept" (No problem) is indicated in a report 100 as a result of inspection of a crack on the inspection location of "STAGE1_ZONE1" of "HPC". Similarly, an endoscope image 112 judged "Accept" (No problem) is also included in the report 100 as a result of inspection of a crack on the same inspection location ("STAGE1_ZONE1" of "HPC").

Further, as a result of inspection of a surface defect on the inspection location of "STAGE1_ZONE1" of "HPC", an endoscope image 113 judged "Re-Inspect" (Reinspection required) is indicated in the report 100.

Further, also as a result of inspection on another inspection location, i.e. as a result of inspection of a crack on the section of "STAGE1_ZONE2" of "HPC", an endoscope image 114 judged "Reject" (Replacement required) is indicated in the report 100.

In other words, the report indicates the endoscope image and the inspection result of its image in a tabular format for each inspection purpose of each inspection location.

(Generation Procedure of Endoscope Inspection Report)

Next, the procedure for generating the report will be described.

A plurality of endoscope images obtained by the user by means of image-picking up is, as described above, recorded in a plurality of folders in the memory card 11. The user generates the report 100 by connecting the PC 43 to the endoscope system 1. At that time, as described above, template information is included in the QR code, and such template information is stored in the memory card 11 during reading of the QR code. The PC 43 reads the report template information from the memory card 11, transmitting the information to the template storage unit 45b of the PC 43.

The PC 43 can read the information in the memory card 11 of the endoscope system 1. The PC 43 runs the report generating program 45a under the instruction of the user to read the information of the folder in the memory card 11 and generate a report. Accordingly, the PC 43 configures an endoscope inspection report generating system. Incidentally, because the memory card 11 is detachably connected to the endoscope system 1, the user may connect the memory card 11 detached from the endoscope system 1 directly to the predetermined interface of the PC 43, thus enabling the PC 43 to read the information of the folder and generate the report.

Figure 19:
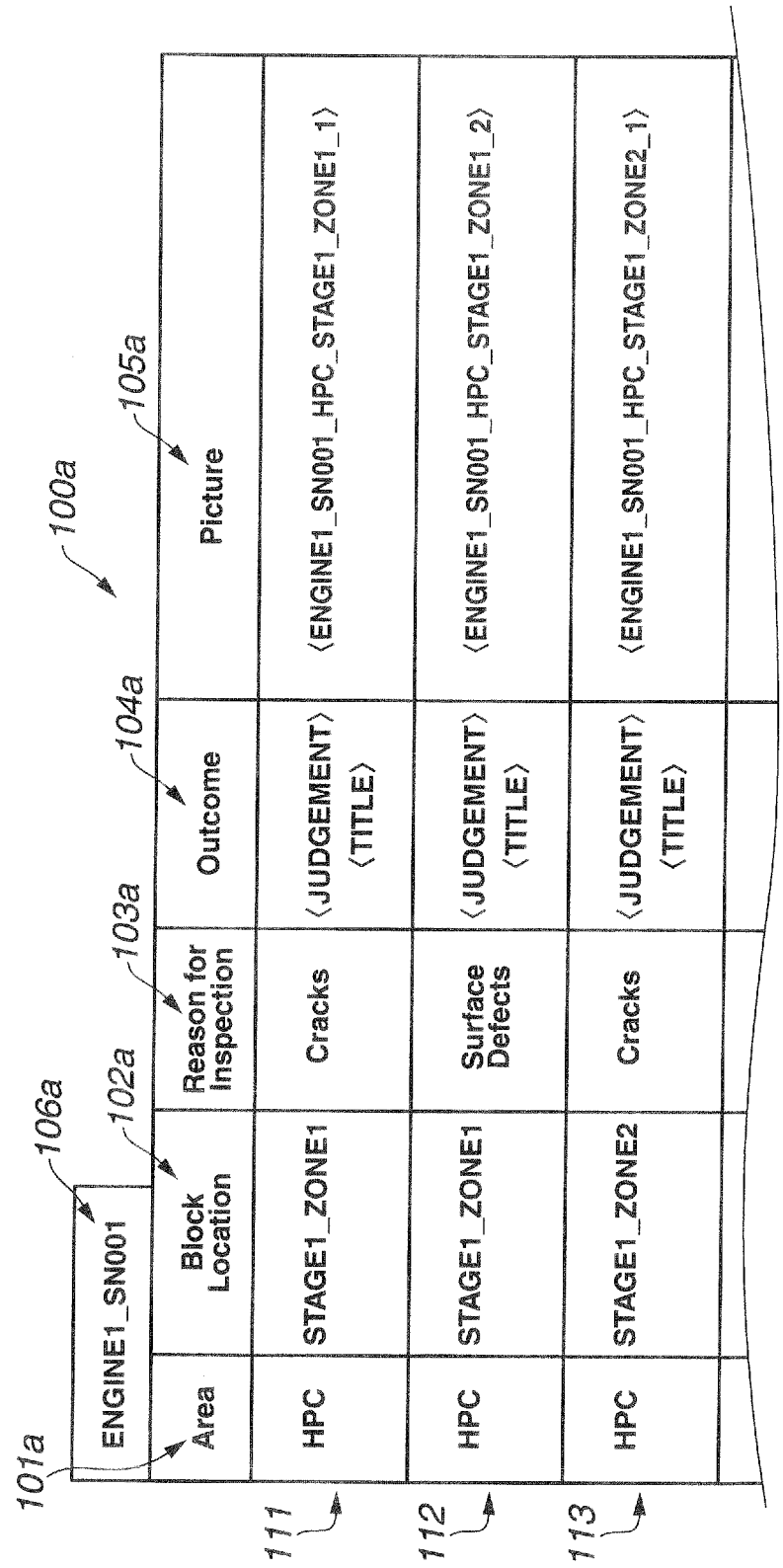
FIG. 19 is a diagram for explaining an example of a report template 100a included in a QR code in accordance with the embodiment of the present invention.

FIG. 19 is a diagram for explaining an example of the report template 100a included in a QR code. FIG. 19 indicates the structure of the report template (hereinafter also referred to simply as template) 100a on the inspection object "ENGINE1_SN001". Since the template in FIG. 19 is the template for the inspection object "ENGINE1_SN001", in the position of the template 100a corresponding to the section 106 of the report in FIG. 18, the character string "ENGINE1_SN001" has been written and set in advance.

Further, because the inspection location of the inspection object is fixed in advance, the character strings "HPC" and "STAGE1_ZONE1" are set in advance in each location of the template 100a corresponding to the sections 101 and 102 of the report in FIG. 18, respectively.

In the section 104a for the inspection result (Outcome) in the template 100a corresponding to the section 104 of the report in FIG. 18, "<JUDGEMENT>" is described and the template 100a is defined so that the character string corresponding to the file mark may be input.

Further, generally the data of the endoscope image are made so that the inspector may additionally input a comment on the image to and record in the image data as additional information of the image. For example, if the endoscope image is the data in an EXIF format, the user may record the comment of the inspector as the metadata in a user comment tag etc. included in the data.

Accordingly, "<TITLE>" is described in the section 104a, and the template 100a is defined so that the recorded comment may be input. Therefore, as shown in FIG. 19, the template 100a is defined with "<TITLE>" also described in the section 104 in addition to "<JUDGEMENT>". A comment will be transcribed to the portion of "<TITLE>".

Because the endoscope image is displayed in the section 105 of the report in FIG. 18, "<ENGINE1_SN001_HPC_STAGE1_ZONE1__1>" is described in the section 105a in FIG. 19, and the template 100a is defined so that the endoscope image may be input.

As shown in FIG. 19, a template defining portion 111 defines the contents of the template on the folder "HPC_STAGE1_ZONE1__1". A template defining portion 112 defines the contents of the template on the folder "HPC_STAGE1_ZONE1__2". A template defining portion 113 defines the contents of the template on the folder "HPC_STAGE1_ZONE2_1".

As above, the contents to be described on a report is defined for each folder in the template included in the QR code attached to the inspection object, and the template defines the predetermined location for each of the inspection result information, the endoscope image and the inspection purpose information in a predetermined report. The image data, the determined result and the metadata for each file obtained by analysis are embedded in a place of the character string in the area sandwiched between "<" and ">" in the template prepared in advance. As a result, the report is generated based on the template as shown in FIG. 18, enabling screen display or printing output.

Incidentally, although description is given with an example of using the template defined so that the data obtained by analyzing the file and the file name may be embedded in the embodiment of the present invention, the template may be one for which only the rule is defined for arranging the inspection target information, the inspection location information, the inspection purpose information and the inspection result information separated with a predetermined mark in an array for each file.

As above, the template for each inspection object is included in the QR code attached to the inspection object. The template information is transmitted to and stored in the template storage unit 45b of the storage device 45. A report is generated by the report generating program 45a based on the template information.

Next, the report generating processing will be described. An endoscope inspection report is generated by the report generating program 45a stored in advance in the storage device 45 of the PC 43.

Figure 20:
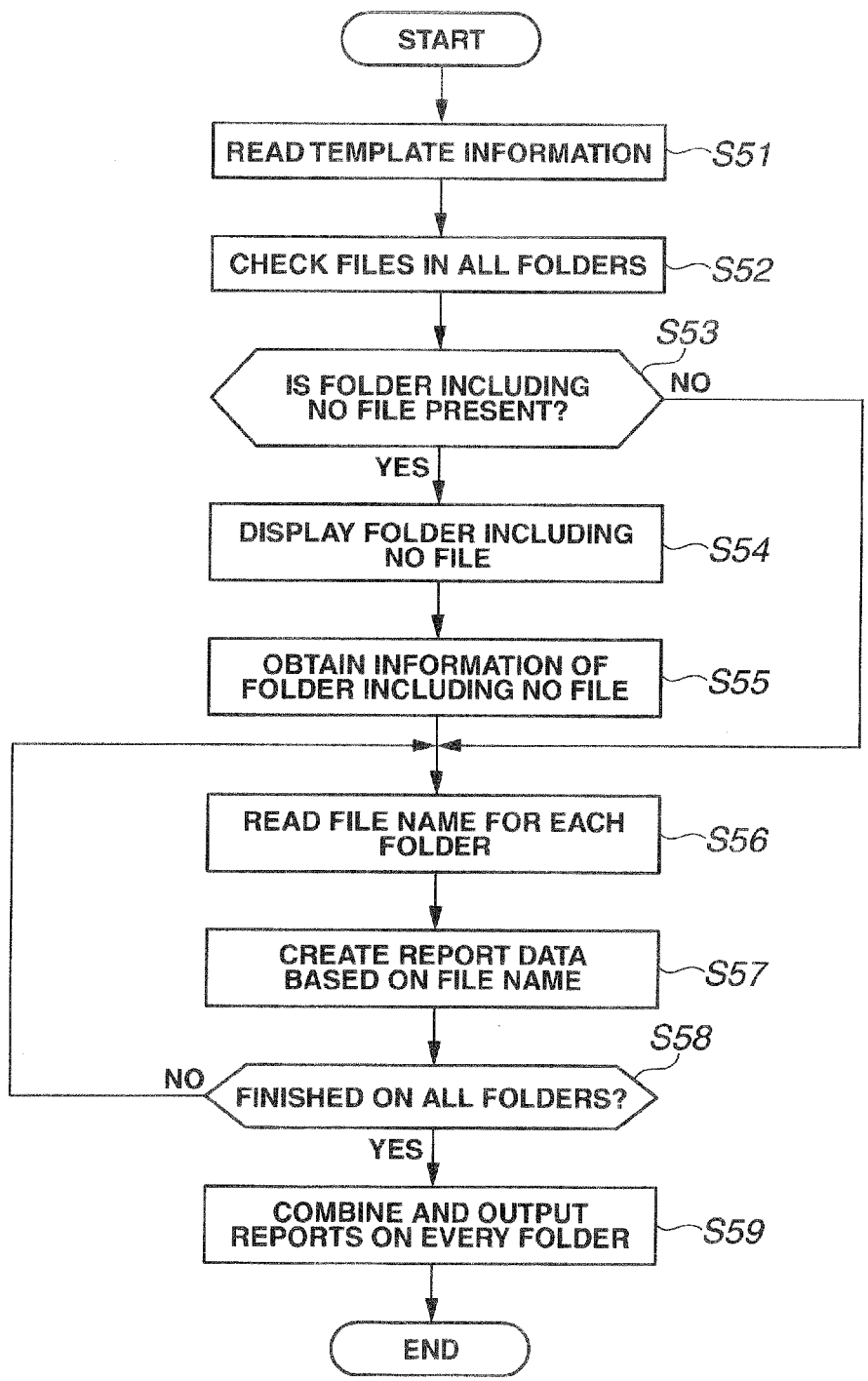
FIG. 20 is a flowchart illustrating an example of flow of generation processing of the endoscope inspection report in accordance with the embodiment of the present invention.

FIG. 20 is a flowchart illustrating an example of flow for generation processing of an endoscope inspection report.

The generation processing of a report will be described below, with a case as an example that the user performs an endoscope inspection of "ENGINE1_SN001" being the inspection object and generates a report using the template 100a as shown in FIG. 19 as a template.

When the user instructs the CPU 43a of the PC 43 to run the report generating program 45a using input means such as the keyboard of the PC 43, the processing in FIG. 20 is started to run.

First, the CPU 43a reads template information transmitted and stored in the template storage unit 45b (S51). In other words, the template information in FIG. 19 is read from the template storage unit 45b of the storage device 45 of the PC 43.

Next, the CPU 43a checks the presence of a file in all folders included in the inspection object, on which a report is to be generated (S52). For example, if the report "ENGINE1_SN001" is generated, in S52, whether a file exists or not is checked for all lower folders included in the folder "ENGINE1_SN001". The S52 processing configures a file presence determining portion for determining the presence of a folder included in each of a plurality of folders.

Next, whether there is a folder not including a file or not is determined (S53). If it is determined that there is a folder not including a file (S53:YES), the CPU 43a displays the folder that includes no file on the screen of the monitor of the PC 43 (S54). At this time, the CPU 43a may determine addition of a file mark on files in all lower folders and display simultaneously any file without a file mark added.

Figure 21:
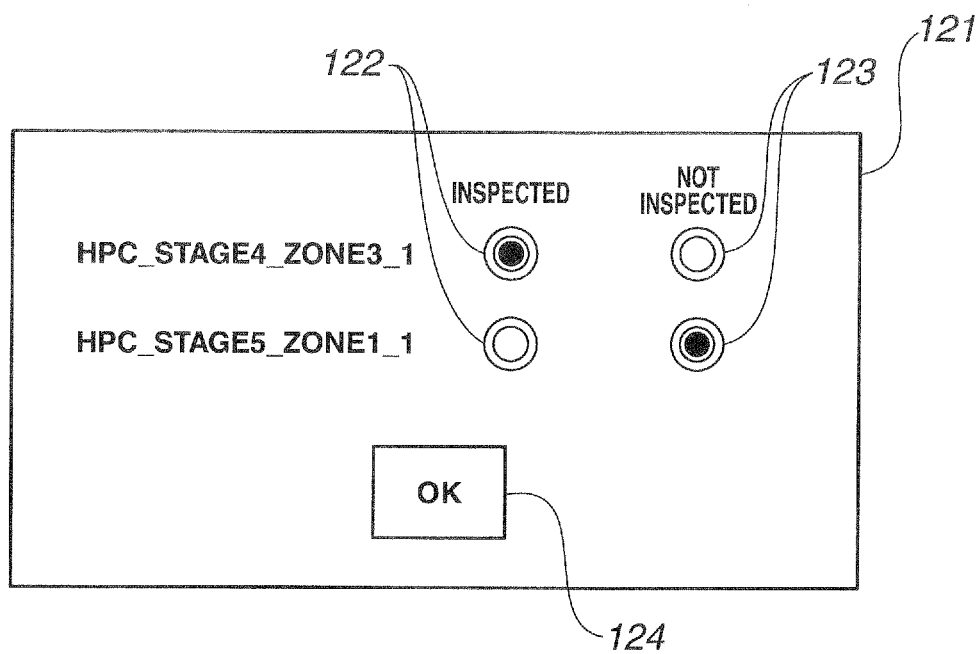
FIG. 21 is a diagram indicating a display example of a pop-up window displaying a folder not including a file in accordance with the embodiment of the present invention.

FIG. 21 is a diagram indicating a display example of a window displaying a folder not including a file. FIG. 21 indicates an example of a different folder structure from the example in FIG. 9, indicating an example of a case where if there are two folders, "HPC_STAGE4_ZONE3_1" and "HPC_STAGE5_ZONE1_1", as folders each not including a file in a plurality of folders included in the inspection object, these two folders are displayed in a window 121.

In the window 121 on an example of FIG. 21, two folders of "HPC_STAGE4_ZONE3_1" and"HPC_STAGE5_ZONE1_1" are displayed as folders not including a file.

Then, in the window 121, check buttons 122 and 123 are displayed to allow inputting of whether the user has not photographed an image at all while an inspection has been performed or whether the inspection itself has not yet been performed, for each folder not including a file. Further, an "OK" button 124 is also displayed in the window 121. The user may select one of the check buttons 122 and 123 by user's designation with an inputting means such as a mouse. In FIG. 21, a black dot is displayed on the check button 122 as checked because the user has designated finish of inspection concerning the folder "HPC_STAGE4_ZONE3_1". Because the user has designated non-inspection concerning the folder "HPC_STAGE5_ZONE1_1", a black dot is displayed on the check button 123 as checked.

If the user selects the "OK" button 124 after the above checking has been performed, the CPU 43a obtains information of the folder not including a file that has been input by the user in the window 121 (S55).

In the case of NO in S53 and after the processing of S55, the CPU 43a reads the file name for each folder (S56) and creates data in the report using the template, based on information of the file name for each file in each folder (S57). Specifically, in the case of "ENGINE1_SN001" as the inspection object, the CPU 43a reads each file out of the folder "HPC_STAGE1_ZONE1_1" in the sequence of serial numbers and writes the character string indicating the inspection result in the section 104a, based on the file mark in the file name of the file that has been read. The CPU 43a further attaches the endoscope image with that file name to the section 105a.

As described above, because the file mark included in the file name of the file that has been read consists of one character here, it is preferable that the inspection result information is converted and written in the section 104 in the report for easier understanding of the user.

Figure 22:
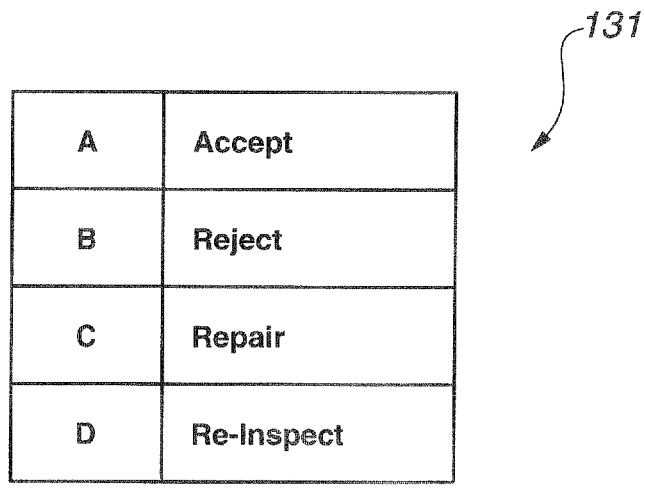
FIG. 22 is a diagram indicating an example of a file mark correspondence table where a character string to be written in a section 104a of the template 100a is stored for each file mark in accordance with the embodiment of the present invention.

FIG. 22 is diagram indicating an example of a file mark correspondence table where the character string to be written in the section 104a of a template 100a is stored for each file mark. The file mark correspondence table in FIG. 22 may either be stored in the storage device 45 or defined in the report generating program 45a.

A file mark correspondence table 131 is a table for converting the inspection result information, including file marks and the character strings corresponding to these file marks. Therefore, the CPU 43a decides the character string corresponding to the file mark in the file name by referring to the file mark correspondence table 131 and writes the character string in the section 104a of the template 100a.

For example, if the file mark in the file name is "A", the character string "Accept" corresponding to "A" will be written in the section 104a of the template 100a. In an example in FIG. 19, the character string "Accept" corresponding to "A" is written in the section 104a, the character string "Reject" corresponding to "B" is written in the section 104a and the character string "Re-Inspect" corresponding to "D" is written in the section 104a. In other words, in S57, inspection result information is converted to predetermined inspection result displaying information and written in the section 104a of the template 100a.

Further, as described above, if the file is provided with a comment, the CPU 43a writes also the comment in the section 104a of the template 100a. FIG. 18 shows examples of comments "Some Defects" and "Cracks" displayed in the section 104.

Besides, the CPU 43a attaches an endoscope image after executing decreasing processing to a predetermined size so that the endoscope image in the file read may be properly placed in the section 105a.

As above, in S56 and S57, the report data are generated based on the file name for the endoscope image in the folder. S56 configures a file name reading portion for reading the file name of an endoscope image, including the inspection result information separated with the predetermined mark or character. Then, S57 configures a report creating portion for creating a predetermined report by writing the inspection result information included in each file name read by the file name reading portion in each predetermined location in the predetermined report, corresponding to the endoscope image with each file name having been read.

Incidentally, although the character string of the inspection purpose information is set for the section 103a because the inspection purpose has been decided in advance for the above described template, the character string indicating the inspection purpose may be created and written from the inspection purpose information included in the file name portion 82. For example, if the inspection purpose information is "1", the "1" is converted to the inspection purpose displaying information of "Cracks" and written in the section 103a.

Similarly, although the character string of the inspection location information is set in the sections of 101a and 102a because the inspection location has been decided for the template as described above, the inspection location information included in the file name portions 81 and 82 may be extracted and the character string of the extracted inspection location information may be written. For example, the character strings of "HPC" and "STAGE1_ZONE1" are extracted from the portions 81 and 82 respectively, and those two extracted character strings of "HPC" and "STAGE1_ZONE1" are written in the sections 101a and 102a, respectively.

The CPU 43a writes each file included in the folder in the section 104a of the template 100a of the inspection result information and attaches the endoscope image of the file name to the section 105a of the template 100a, based on the file name. The S56 and S57 processing is executed for all the files in one folder.

When the S57 processing is finished, the CPU 43a determines whether execution of the above processing has been finished for all the folders (S58). This is for the purpose of executing the same processing also for other folders when the S56 and S57 processing is finished for one folder if there are a plurality of folders included in the inspection object.

If the above processing has not been executed for all the folders (S58:NO), the processing returns to S56, and the S56 and 57 processing is executed for other folders for which the processing has not been executed.

Incidentally, concerning the folder on which the inspection as described in FIG. 21 has been finished and which does not include an endoscope image, the CPU 43a embeds either the characters of "No image" in the section 105 or an image with characters of "NO PHOTO" etc. Besides, concerning an uninspected folder, the character of "Uninspected" is embedded in the section 105.

Figure 23:
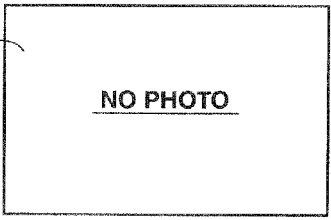
FIG. 23 is a diagram for explaining a display example of both an inspected folder not including an endoscope image and an uninspected folder in a report in accordance with the embodiment of the present invention.

FIG. 23 is a diagram for explaining a display example of both the inspected folder not including an endoscope image and the uninspected folder. FIG. 23 is a display example on the folder indicated in FIG. 21.

As shown in FIG. 23, concerning the folder "HPC_STAGE4_ZONE3_1", an image 115 with the characters of "NO PHOTO" is attached, together with "Accept" written in the section 104a. Concerning the folder "HPC_STAGE5_ZONE1_1", a character 116 of "Uninspected" is written in the section 105a. In other words, if a folder not including a file has been detected by S52, the no file information indicating that the folder does not include a file is written in the report in S57. The no file information is, for example, the characters "No Image", an image with the characters of "NO PHOTO" or the character "Uninspected".

As above, when processing for all the folders has been finished (S58:YES), the report 100 is output as shown in FIGS. 18 and 23 that is generated as the other file than the template 100a with the contents in each section from 101a to 105a for each folder combined (S59). The data of the output report 100 are stored in the storage device 45, which will then be displayed on the monitor 43 or output to a printer.

In other words, a plurality of endoscope images obtained in an endoscope inspection are stored in a plurality of folders separated for each inspection purpose information, and in S56 and S57, an endoscope image and inspection result information with each file name are written in a predetermined location in the report in the unit of folder.

Therefore, when designating the folder subject to inspection to run the report generating program 45a in the PC 43 after an endoscope inspection has been performed, the user may generate the endoscope inspection report as shown in FIGS. 18 and 23 automatically.

According to the above described embodiment, the user may create the endoscope inspection report easily without performing complicated works of viewing and attaching each endoscope image onto the report in a predetermined format and at the same time copying or inputting the determined result of that image as in the past.

Incidentally, although the endoscope inspection report is created by the PC 43 in the above example, the report may be created in the endoscope system 1. In such a case, the report is created in such a way that the report creating processing program 45a and the template information are stored in the ROM 22 of the endoscope system 1, which is an endoscope inspection report creating system, or in the memory card 11 and the CPU 21 runs that program.

Next, a modification of report generation will be described.

The sequence of attaching inspected images in the report is decided in advance in the template included in the above described QR code, but in this modification, it is possible to change the sequence of attaching inspected images in the report to be created to make it different from the inspection sequence in the template.

While the folder structure included in the QR code is consistent with the inspection sequence determined in consideration of inspection efficiency, the inspection sequence and the sequence of attaching inspected images to the report may not be always the same. Therefore, there may be a case where the sequence of attaching inspected images in the report defined in the template is desired to be changed.

Therefore, in this modification, the information on the sequence of attaching inspected images is included in the QR code in addition to the folder information and the template information, and the report generating program 45a changes the sequence of attaching inspected images in the report using the information on the sequence of attaching inspected images. In other words, the QR code included in the image obtained by image-picking up with the image pickup portion includes the information indicating the sequence of attaching a plurality of image data to the report template. Incidentally, the description is provided here with a case of the number of inspection items being three, for making the explanation easier.

FIG. 24 is a diagram for explaining an example of a report template included in a QR code in accordance with this modification. The template 200a shown in FIG. 24 is a report template on the inspection object "ENGINE1_SN001", where "<AREA1>", "<AREA2>" and "<AREA3>" are described in the position of the section 101a corresponding to the section 101 of the report in FIG. 18; and "<LOCATION1>", "<LOCATION 2>" and "<LOCATION 3>" are described in the position of the section 102a corresponding to the section 102 of the report in FIG. 18. Similarly, "<INSPECTION1>", "<INSPECTION 2>" and "<INSPECTION 3>" are described in the position of the section 103a corresponding to the section 103 of the report in FIG. 18.

In the section 104a for the inspection result (Outcome) in the template 200a corresponding to the section 104 of the report in FIG. 18, "<JUDGEMENT1>", "<JUDGEMENT2>" and "<JUDGEMENT3>" are described and the template 200a is defined so that the character string corresponding to the file mark may be input. Further, in the section 104a, "<TITLE1>", "<TITLE2>" and "<TITLE3>" are described, and the template 200a is defined so that the recorded comment may be input.

Since an endoscope image is displayed in the section 105 of the report in FIG. 18, in the section 105a of the report in FIG. 24, "<PIC1>", "<PIC 2>" and "<PIC 3>" are described, and the template 200a is defined so that the image data may be input.

As shown in FIG. 24, the template defining portion 111 defines the contents of the template on "<LOCATION1>" of the inspection location "<AREA1>". The template defining portion 112 defines the contents of the template on "<LOCATION2>" of the inspection location "<AREA2>". The template defining portion 113 defines the contents of the template on "<LOCATION3>" of the inspection location "<AREA3>".

Figure 25:
FIG. 25 is a diagram for explaining an example of information on a sequence of attaching inspected images included in the QR code in accordance with the modification of the embodiment of the present invention.

FIG. 25 is a diagram for explaining an example of information on the sequence of attaching inspected images included in a QR code in accordance with this modification. As shown in FIG. 25, the sequence information TBL for attaching inspected images (hereinafter referred to as attachment sequence information) is table information, which includes the inspection sequence, the inspection item in each inspection sequence and the report attachment sequence in each inspection sequence.

For example, the attachment sequence information TBL indicates that the inspection item "HPC_STAGE_ZONE2_1" of the inspection sequence 3 is 1 in the report attachment sequence, the inspection item "HPC_STAGE_ZONE1_1" of the inspection sequence 1 is 2 in the report attachment sequence and the inspection item "HPC_STAGE_ZONE1_2" of the inspection sequence 2 is 3 in the report attachment sequence.

FIG. 26 is a diagram for explaining an example of the structure of an endoscope inspection report generated with report template information in FIG. 24 and the attachment sequence information TBL in FIG. 25. As shown in FIG. 26, the inspected image attachment sequence in the report to be generated has been changed to make it different from the inspection sequence in the template, based on the attachment sequence information TBL in FIG. 25.

Incidentally, although one section has been set for one inspection item and a plurality of image data are attached in one section in FIG. 26, one image data may be attached in one section. In such a case, the character string such as the inspection location or the inspection purpose is also written in each section.

The attachment sequence information TBL in FIG. 25 is read together with folder information (including template information) when the QR code is read in the folder generation processing in the above described FIG. 4. Then, the attachment sequence information TBL having been read is transmitted to the memory card 11 and stored as one file together with the folder information after being temporarily stored in the RAM 23.

The processing that an endoscope inspection is performed and an inspected image is stored in each corresponding folder is the same as the processing described in the above embodiment.

Figure 27:
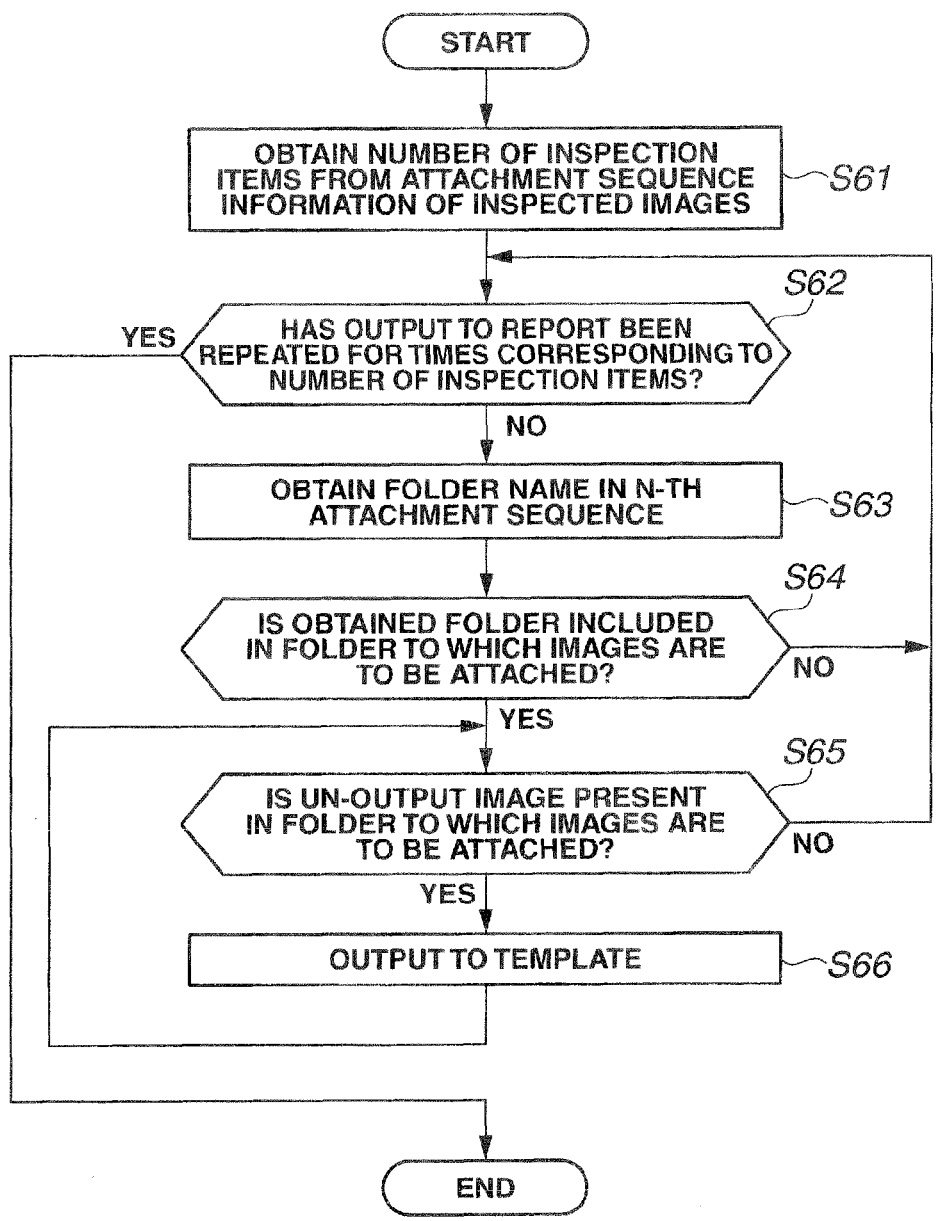
FIG. 27 is a flowchart illustrating an example of flow of generation processing of a report in accordance with the modification of the embodiment of the present invention.

FIG. 27 is a flowchart illustrating an example of flow of generation processing of a report in accordance with this modification. Report generation processing runs, for example, the report generating program 45a of the PC 43 under the instruction of the user to read the folder information, the template information and the attachment sequence information TBL in the memory card 11, generating a report based on the folder information, the template information and the attachment sequence information TBL.

The processing from S56 to S59 in FIG. 20 is replaced by the processing as shown in FIG. 27.

First, the CPU 43a obtains the number of inspection items from the attachment sequence information TBL (S61). The number of inspection items may be obtained, for example, from the inspection sequence information. In case of FIG. 25, it is 3.

Successively, the CPU 43a determines whether output to the report template has been repeated for times corresponding to the number of inspection items (S62). If not repeated three times (S63:NO), the folder name in the n-th attachment sequence is obtained (S63). Incidentally, the initial value of n is 1, which will be incremented by one if the processing after S63 is executed.

If for the first time, S62 results in NO and the folder name in the 1st attachment sequence is obtained from the attachment sequence information TBL, and the CPU 43a determines whether the obtained folder is included in the folder to which an image is to be attached (i.e. the folder subject to inspection) (S64). If the obtained folder is not included in the folder to which an image is to be attached (S64:NO), the processing returns to S62. In other words, if the folder name included in the attachment sequence information TBL is not present in any of the folders included in the inspection object on which a report is to be generated, S62 results in NO.

If the obtained folder is included in the folder to which an image is to be attached (S64:YES), whether there is an image file that has not been output to the folder to which an image is to be attached (i.e. a folder subject to inspection) or not (i.e. an image file that has not been output to the report template) is determined (S65). If there is no image file that has not been output to the folder to which an image is to be attached (S65:NO), the processing returns to S62. In other words, if there is no image file that has not been output to the folder to which an image is to be attached, S65 results in NO.

If there is an image file that has not been output to the folder to which an image is to be attached (i.e. a folder subject to inspection) (i.e. an image file that has not been output to the report template) (S65:YES), the image file is output to the report template (S66), and the processing returns to S64. In output of an image file to the report template in S66, writing and conversion of the character string as well as attachment of the image are performed from each file name to each definition.

If the processing from S64 to S66 is executed and S64 or S65 results in NO, the processing returns to S62, and the processing from S63 to S66 is executed for the next inspection item.

Since the number of inspection items is 3 in the case of FIG. 25, if the processing from S64 to S66 is executed for the folder name in the third attachment sequence, the processing is finished with S62 resulting in YES. Through the above processing, the report in FIG. 26 is generated.

According to this modification, because the report template becomes independent of the inspection sequence, the report template may be made a template that can be commonly used for a plurality of inspection objects.

Incidentally, the attachment sequence information, because of relatively less information, may also be written in the EXIF information in the image file during image pickup of an inspection image. In this case, in reference to the contents of the file of attachment sequence information during image pickup of the inspection image, the inspected image attachment sequence corresponding to the selected folder is written sequentially in the EXIF information in the image file. Then, the inspected image attachment sequence has only to be written in the report template in the order of earlier sequence by referring to the EXIF information in each image file during the report generation.

If such a structure is made, it is not necessary to transmit the attachment sequence information to the PC 43 for reference during the report generation.

Incidentally, although the report template is in a tabular format in the above described embodiment and modification, the template may not necessarily be in a tabular format.

Figure 28:
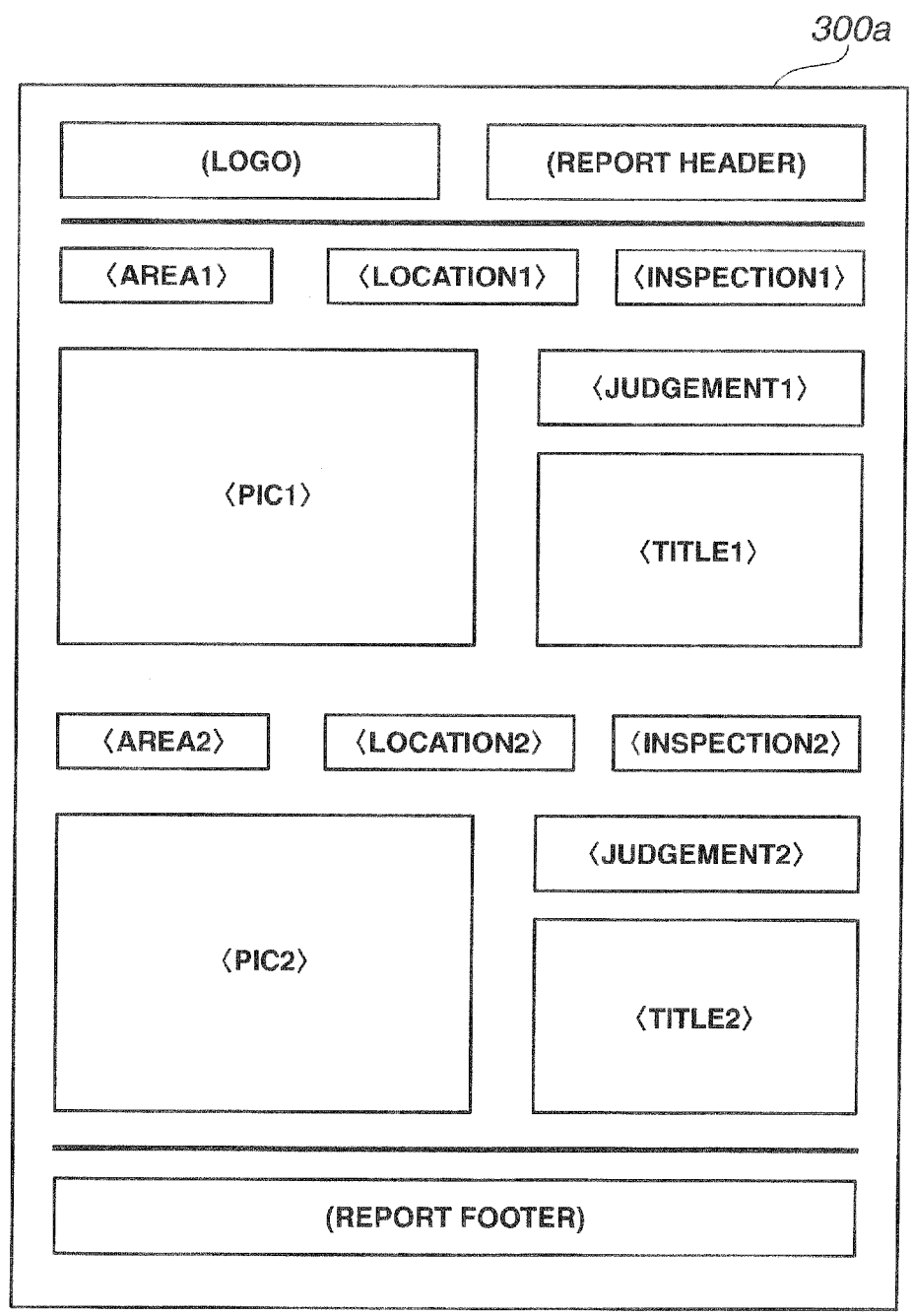
FIG. 28 is a diagram indicating another example of a report template structure in accordance with the embodiment of the present invention.

FIG. 28 is a diagram indicating another example of a report template structure. As shown in FIG. 28, the report does not have a tabular format structure, but has a structure of the inspection location, the inspection purpose, the endoscope image, etc. being disposed in the predetermined location. Further, the report is structured to include, for example, information such as the logo of a company, the header and the footer.

Incidentally, the report template may be structured so that the report may include the information such as date, location name, inspector's name, manufacturing number, conclusion of a test and summary as additional inspection information.

As above, in an endoscope inspection, it is possible to record the image data of endoscope images, without fail, in a plurality of folders corresponding to the inspection object and also to generate the report in accordance with the proper template corresponding to the inspection object, by including information of the report template in the QR code in addition to the information of the folder structure.

Incidentally, although a sticker etc. printed with the QR code TDC is attached to the housing OB etc. of the inspection object in the above described embodiment, the QR code TDC may be printed in the manual, the inspection card, etc. for the inspection object, or a sticker etc. printed with the QR code TDC may be attached to the inspection object.

Still further, although a QR code is used in the above described example, any other two-dimensional code than the QR code may be used.

Besides, instead of a two-dimensional code, coded information of a normal barcode etc. or character information may be used as the inspection object identifying information. In such a case, if the information content of coded information or character information is little, a plurality of folder information corresponding to the coded information is stored in advance in the ROM 22, and the image obtained by image-picking up with the image pickup unit 41 is analyzed, by which the coded information etc. is extracted. Then, the folder information corresponding to the inspection object may be obtained by reading the folder information corresponding to the extracted coded information etc. from the ROM 22, which is a memory.

Further, instead of keeping a plurality of folder information corresponding to the coded information stored in advance in the ROM 22 according to the number of the inspection object, if the endoscope system 1 can access the network environment such as the Internet, a plurality of folder information corresponding to the coded information may be kept stored in advance according to the number of the inspection object in a system such as a server that exists in the network environment. In such a case, the endoscope system 1 may access the folder information corresponding to the extracted coded information etc. on the server etc. via the network environment and obtain the folder information corresponding to the inspection object from the server.

As above, according to the above described embodiment or modification, an endoscope system, a folder generating method for recording an endoscope image and a program may be provided that are capable of generating a proper folder without fail for recording endoscope images obtained by image-picking up in endoscope inspection according to the inspection object.

Still further, the program code of software for running the above described operations is kept recorded or stored, as a computer program product, in its entirety or in part on a portable medium such as a flexible disk and a CD-ROM or on a nontemporary computer readable medium such as a storage device of a hard disk. The program code is read by a computer and the entirety or part of operation is executed. Or, the entirety or part of the program may be distributed or provided via the communication network. The user may easily implement the endoscope system and the folder generating method for recording an endoscope image of the present invention by downloading the program via the communication network and installing in a computer or installing the program in a computer from a storage medium.

Each "portion or unit" in this specification is conceptual corresponding to each function of embodiments, which does not necessarily correspond one to one to a specific hardware or software routine. Therefore, in this specification, embodiments have been described in supposition of a virtual circuit block (portion or unit) having each function of embodiments. Further, each step of each procedure in an embodiment may be changed in its execution sequence, a plurality of procedures may be simultaneously executed or each execution may have a different execution sequence provided that those do not contradict its property.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. An endoscope apparatus comprising:
    an image pickup portion configured to pick up an image containing folder generating information in a folder generating mode, and to pick up image data of an inspection object in an inspection mode;

an analyzing portion configured to analyze the image picked up by the image pickup portion in the folder generating mode, and to extract from the analyzed image a folder name contained in the folder generating information;

a folder generating portion configured to generate a folder in a memory, and to set the folder name extracted by the analyzing portion as a name of the folder;

an image recording portion configured to record in the folder generated by the folder generating portion the image data of the inspection object picked up by the image pickup portion in the inspection mode; and a display portion configured to display an image of the inspection object based on the image data of the inspection object picked up by the image pickup portion in the inspection mode, wherein the display portion is configured to display an indication when the folder generating information is not included in the image picked up by the image pickup portion in the folder generating mode.

2. The endoscope apparatus according to claim 1, wherein the display portion is configured to display a guide for obtaining the folder generating information in the folder generating mode.

3. The endoscope apparatus according to claim 1, further comprising an operating portion configured to designate the folder generated by the folder generating portion to be displayed on the display portion.

4. The endoscope apparatus according to claim 1, wherein the folder name includes a name of the inspection object.

5. The endoscope apparatus according to claim 1, wherein the analyzing portion is further configured to extract report template information from the analyzed image, and to generate a report template from the report template information.

6. The endoscope apparatus according to claim 5, wherein the extracted report template information includes information indicating a sequence of attaching a plurality of image data to the report template.

7. The endoscope apparatus according to claim 1, wherein the analyzing portion analyzes a two-dimensional code in the image picked up by the image pickup portion in the folder generating mode, the two-dimensional code including the folder generating information.

* * * * *